United States Patent
Ito

(10) Patent No.: US 11,096,807 B2
(45) Date of Patent: Aug. 24, 2021

(54) MEDICAL INSTRUMENT HAVING HYDROPHILIC MEMBER AND HYDROPHOBIC MEMBER STACKED

(71) Applicant: TERUMO KABUSHIKI KAISHA, Tokyo (JP)

(72) Inventor: Takashi Ito, Shizuoka (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 0 days.

(21) Appl. No.: 16/520,846

(22) Filed: Jul. 24, 2019

(65) Prior Publication Data
US 2019/0343665 A1 Nov. 14, 2019

Related U.S. Application Data

(63) Continuation of application No. PCT/JP2018/012137, filed on Mar. 26, 2018.

(30) Foreign Application Priority Data

Mar. 30, 2017 (JP) .............................. JP2017-068897

(51) Int. Cl.
*A61F 2/90* (2013.01)
*A61B 17/12* (2006.01)
(Continued)

(52) U.S. Cl.
CPC .......... *A61F 2/90* (2013.01); *A61B 17/12113* (2013.01); *A61L 31/08* (2013.01);
(Continued)

(58) Field of Classification Search
CPC ................. A61F 2/90; A61F 2002/823; A61F 2210/0076; A61F 2250/0067; A61F 2/91;
(Continued)

(56) References Cited

U.S. PATENT DOCUMENTS

| 5,102,401 A | 4/1992 | Lambert et al. |
| 5,554,180 A | 9/1996 | Turk |

(Continued)

FOREIGN PATENT DOCUMENTS

| CN | 1717263 A | 1/2006 |
| CN | 1812754 A | 8/2006 |

(Continued)

OTHER PUBLICATIONS

International Search Report (PCT/ISA/210) dated Jun. 5, 2018, by the Japan Patent Office as the International Searching Authority for International Application No. PCT/JP2018/012137.
(Continued)

*Primary Examiner* — George J Ulsh
*Assistant Examiner* — Rachel S Highland
(74) *Attorney, Agent, or Firm* — Buchanan Ingersoll & Rooney PC

(57) ABSTRACT

A medical instrument is disclosed having a structure capable of preventing liquid circulation between an inner layer side and an outer layer side of a peripheral wall portion. The medical instrument includes a main body portion in which a center hole and a radially outward space are partitioned by a tubular peripheral wall portion. The peripheral wall portion includes at least a first layer on which a hydrophilic member, in which a hydrophilic coating is formed on a first base portion, is disposed and a second layer on which a hydrophobic member, in which a hydrophobic coating is formed on a second base portion, is disposed. The peripheral wall portion is configured by the first layer and the second layer being stacked along a radial direction. As a result of swelling of the hydrophilic coating, the adjacent hydrophilic members come into contact with each other.

19 Claims, 20 Drawing Sheets

(51) Int. Cl.
*A61L 31/08* (2006.01)
*A61L 31/16* (2006.01)
*A61B 17/00* (2006.01)

(52) U.S. Cl.
CPC ......... *A61L 31/16* (2013.01); *A61B 17/12177* (2013.01); *A61B 2017/00938* (2013.01); *A61B 2017/00942* (2013.01)

(58) Field of Classification Search
CPC .......... A61F 2/958; A61L 31/08; A61L 31/16; A61L 2400/10; A61L 29/085; A61L 29/14; A61L 29/16; A61B 17/12113; A61B 17/12177; A61B 2090/3966; A61B 2017/00938; A61B 2017/00942; A61B 17/12118; A61M 25/00; A61M 25/06; A61M 25/10
See application file for complete search history.

(56) References Cited

U.S. PATENT DOCUMENTS

| | | | |
|---|---|---|---|
| 6,117,168 | A | 9/2000 | Yang et al. |
| 6,458,867 | B1 * | 10/2002 | Wang ............... A61L 29/085 523/105 |
| 2004/0167597 | A1 | 8/2004 | Costantino et al. |
| 2005/0021131 | A1 | 1/2005 | Venkatraman et al. |
| 2005/0171572 | A1 | 8/2005 | Martinez |
| 2006/0045901 | A1 * | 3/2006 | Weber ............... A61L 31/16 424/426 |
| 2007/0060994 | A1 | 3/2007 | Gobran et al. |
| 2008/0004546 | A1 | 1/2008 | Kato |
| 2009/0093871 | A1 | 4/2009 | Rea et al. |
| 2010/0070015 | A1 | 3/2010 | Schneider et al. |
| 2010/0324667 | A1 | 12/2010 | King |
| 2011/0169198 | A1 | 7/2011 | DeSimone et al. |
| 2012/0265100 | A1 | 10/2012 | Maki |
| 2013/0012967 | A1 | 1/2013 | Tani et al. |
| 2015/0088101 | A1 | 3/2015 | Takada |
| 2017/0333231 | A1 | 11/2017 | Li |

FOREIGN PATENT DOCUMENTS

| | | |
|---|---|---|
| CN | 101827567 A | 9/2010 |
| CN | 101978934 A | 2/2011 |
| CN | 102307547 A | 1/2012 |
| CN | 102711675 A | 10/2012 |
| CN | 102743813 A | 10/2012 |
| CN | 103566418 A | 2/2014 |
| CN | 104436412 A | 3/2015 |
| CN | 204542477 U | 8/2015 |
| JP | H04226670 A | 8/1992 |
| JP | 2001513660 A | 9/2001 |
| JP | 2007082943 A | 4/2007 |
| JP | 2008011938 A | 1/2008 |
| JP | 2008012276 A | 1/2008 |
| JP | 2012070979 A | 4/2012 |
| JP | 2015062512 A | 4/2015 |
| JP | 2015181723 A | 10/2015 |

OTHER PUBLICATIONS

Written Opinion (PCT/ISA/237) dated Jun. 5, 2018, by the Japan Patent Office as the International Searching Authority for International Application No. PCT/JP2018/012137.

An English Translation of the International Search Report (Form PCT/ISA/210) and the Written Opinion of the International Searching Authority (Form PCT/ISA/237) dated Jun. 5, 2018, by the Japanese Patent Office in corresponding International Application No. PCT/JP2018/012137. (6 pages).

Office Action (Notification of the First Office Action) dated Dec. 31, 2020, by the National Intellectual Property Administration, PRC in corresponding Chinese Patent Application No. 201880005207.4 and an English Translation of the Office Action. (13 pages).

* cited by examiner

MEDICAL INSTRUMENT HAVING HYDROPHILIC MEMBER AND HYDROPHOBIC MEMBER STACKED

CROSS-REFERENCES TO RELATED APPLICATIONS

This application is a continuation of International Application No. PCT/JP2018/012137 filed on Mar. 26, 2018, which claims priority to Japanese Application No. 2017-068897 filed on Mar. 30, 2017, the entire content of both of which is incorporated herein by reference.

FIELD OF THE DISCLOSURE

The present disclosure relates to a medical instrument having a hydrophilic member and a hydrophobic member stacked.

BACKGROUND DISCUSSION

Hydrophilic and hydrophobic coatings are used in the field of medical instruments.

For example, the guide wire that is described in JP-A-2015-62512 forms an air gap between hydrophilic and hydrophobic coating films and keeps moisture in the air gap. As a result, the guide wire exhibits lubricity even in a situation in which the amount of the surrounding water is relatively small.

Hydrophilic and hydrophobic polymer wires are spirally wound on the surface of the main body of the guide wire described in JP-A-2015-181723. As a result, the guide wire exhibits slidability in both dry and wet environments.

In each of the guide wires that are described in JP-A-2008-12276, JP-A-2008-11938, and JP-A-2007-82943, the coil portion at the distal end of the wire has an airtight structure. The coating film that covers the coil portion is formed by lamination of a hydrophobically coated first layer and a hydrophilically coated second layer. As a result, the coil portion of the guide wire receives buoyancy and drooping of the distal portion attributable to gravity can be prevented.

SUMMARY

In the medical field, existing hydrophilic and hydrophobic coatings are used simply for helping ensure lubricity or forming a coating film.

In accordance with an exemplary embodiment, liquid circulation between the inner and outer layer sides of a tubular peripheral wall portion can be prevented by constituting the peripheral wall portion by means of lamination of a layer on which a hydrophilic member is disposed and a layer on which a hydrophobic member is disposed, which can be made to medical instrument diameter reduction and performance improvement once the configuration is applied to a medical instrument.

In accordance with an exemplary embodiment, a medical instrument is disclosed having a novel structure capable of preventing liquid circulation between an inner layer side and an outer layer side of a peripheral wall portion.

In accordance with an exemplary embodiment, a medical instrument is disclosed, which includes a main body portion in which a center hole and a radially outward space are partitioned by a tubular peripheral wall portion. The peripheral wall portion includes at least a first layer having a hydrophilic member including a first base portion and a hydrophilic coating formed on the first base portion; and a second layer having a hydrophobic member including a second base portion and a hydrophobic coating formed on the second base portion. The peripheral wall portion is formed by stacking the first layer and the second layer along a radial direction. When the hydrophilic coating is swollen, the adjacent hydrophilic members come into contact with each other so that a first liquid in the center hole and a second liquid present in the radially outward space are prevented from circulating through the peripheral wall portion.

In accordance with an exemplary embodiment, a medical instrument is disclosed comprising: a main body portion having a center hole and a radially outward space partitioned by a tubular peripheral wall portion; the tubular peripheral wall portion including at least: a first layer having a hydrophilic member including a first base portion and a hydrophilic coating formed on the first base portion; a second layer having a hydrophobic member including a second base portion and a hydrophobic coating formed on the second base portion; the first layer and the second layer being stacked along a radial direction; and wherein when the hydrophilic coating is swollen, adjacent hydrophilic members come into contact with each other so that a first liquid in the center hole and a second liquid present in the radially outward space are prevented from circulating through the tubular peripheral wall portion.

In accordance with another exemplary embodiment, a medical instrument comprising: an elongated tubular peripheral wall portion having a central lumen, the tubular peripheral wall portion including at least: a first braided layer having a hydrophilic member including a first base portion and a hydrophilic coating formed on the first base portion; and a second braided layer having a hydrophobic member including a second base portion and a hydrophobic coating formed on the second base portion, and wherein the first braided layer and the second braided layer are stacked along a radial direction.

In accordance with a further exemplary embodiment, a medical instrument is disclosed comprising: a main body portion having a lumen and a radially outward space partitioned by a tubular peripheral wall portion; the tubular peripheral wall portion including at least: a first layer having a hydrophilic member including a first base portion and a hydrophilic coating formed on the first base portion; a second layer having a hydrophobic member including a second base portion and a hydrophobic coating formed on the second base portion; the first layer and the second layer being stacked along a radial direction, and wherein one of the first layer and the second layer is coiled shape, and another of the first layer and the second layer is mesh shaped; and wherein when the hydrophilic coating is swollen, adjacent hydrophilic members come into contact with each other so that a first liquid in the lumen and a second liquid present in the radially outward space are prevented from circulating through the tubular peripheral wall portion.

In the medical instrument configured as described above, when the hydrophilic coating is swollen, the adjacent hydrophilic members come into contact with each other so that the first liquid in the center hole and the second liquid present in the radially outward space can be prevented from circulating through the peripheral wall portion.

DETAILED DESCRIPTION

Figure 1A:
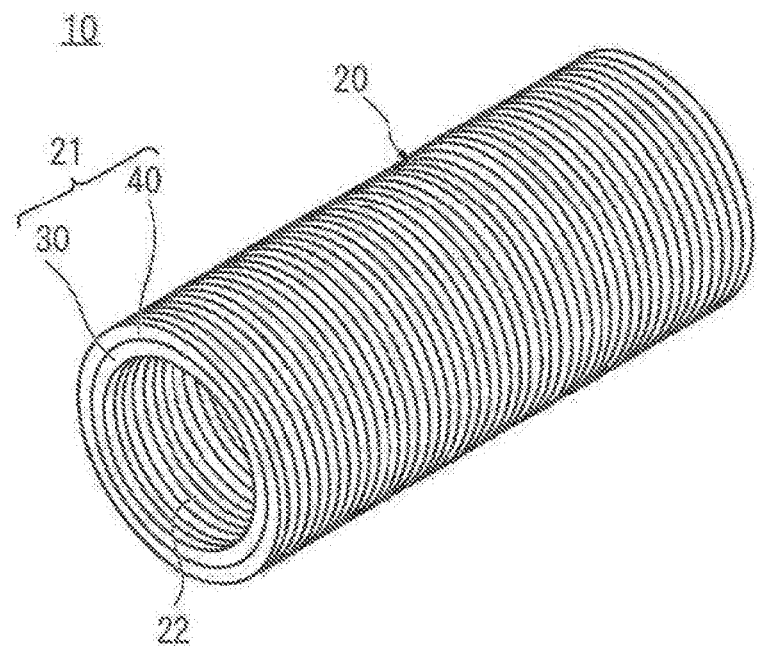
FIG. 1A is a perspective view illustrating the basic structure of a medical instrument having a tubular main body portion.

Hereinafter, an embodiment of the disclosure will be described with reference to accompanying drawings. The following description does not limit the technical scope or the meaning of terms described in the claims. In the drawings, dimensional ratios are exaggerated for convenience of description. The dimensional ratios may differ from actual ratios.

Figure 1B:
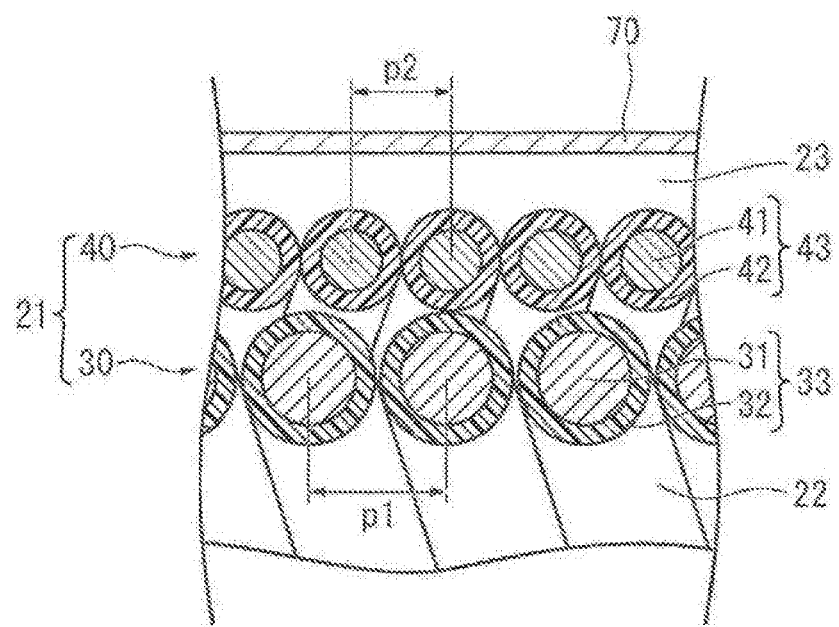
FIG. 1B is a cross-sectional view of a main part illustrating a state where a hydrophilic coating is yet to swell.
Figure 1C:
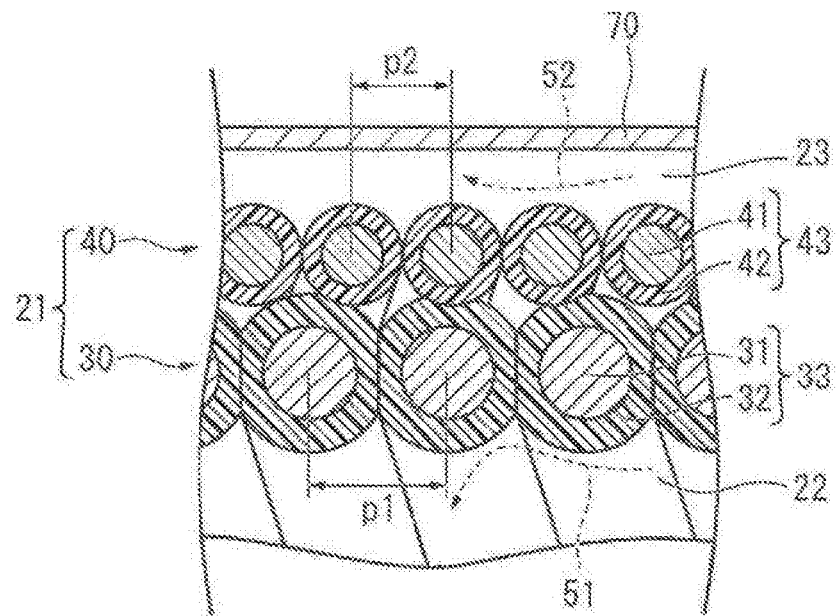
FIG. 1C is a cross-sectional view of a main part illustrating a state where adjacent hydrophilic members are in contact with each other as a result of swelling of the hydrophilic coating.
Figure 1D:
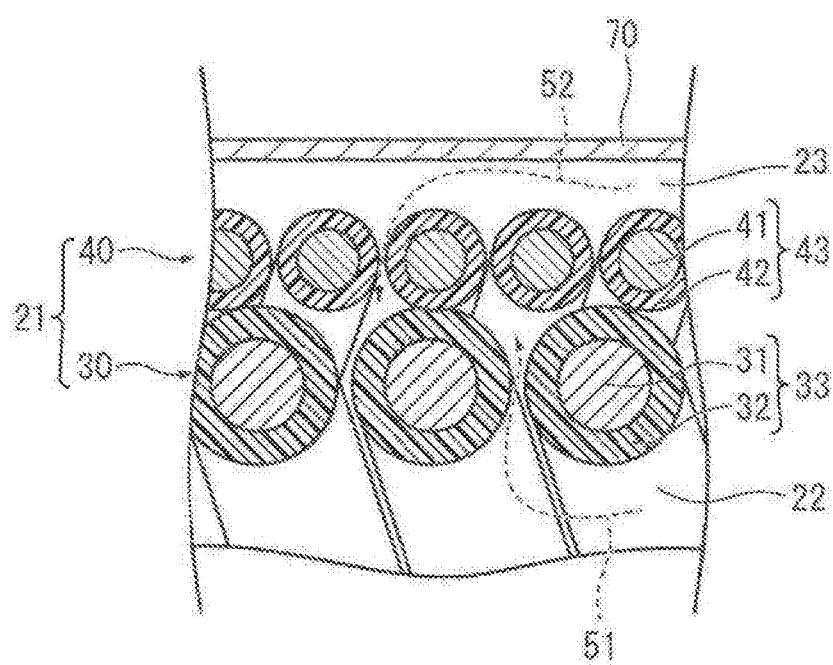
FIG. 1D is a cross-sectional view of a main part illustrating a state where the main body portion is expanded with the hydrophilic coating swollen.

FIG. 1A is a perspective view illustrating the basic structure of a medical instrument 10 having a tubular main body portion 20, FIG. 1B is a cross-sectional view of a main part illustrating a state where a hydrophilic coating 32 is yet to swell, and FIG. 1C is a cross-sectional view of a main part illustrating a state where adjacent hydrophilic members 33 are in contact with each other as a result of swelling of the hydrophilic coating 32. FIG. 1D is a cross-sectional view of a main part illustrating a state where the main body portion 20 is expanded with the hydrophilic coating 32 swollen.

The basic structure of the medical instrument 10 will be outlined with reference to FIGS. 1A to 1D. In accordance with an exemplary embodiment, the medical instrument 10 has the main body portion 20, in which a center hole 22 and a radially outward space 23 are partitioned by a tubular peripheral wall portion 21. The peripheral wall portion 21 includes at least a first layer 30 on which the hydrophilic member 33, in which the hydrophilic coating 32 is formed on a first base portion 31, is disposed and a second layer 40 on which a hydrophobic member 43, in which a hydrophobic coating 42 is formed on a second base portion 41, is disposed. The peripheral wall portion 21 is formed by stacking the first layer 30 and the second layer 40 along a radial direction. As a result of swelling of the hydrophilic coating 32, the adjacent hydrophilic members 33 come into contact with each other and a first liquid 51 in the center hole 22 and a second liquid 52 present in the radially outward space 23 can be prevented from circulating through the peripheral wall portion 21 (see FIG. 1C). Once the space between the adjacent hydrophilic members 33 and the space between the adjacent hydrophobic members 43 are expanded, the first liquid 51 and the second liquid 52 circulate through the peripheral wall portion 21 (see FIG. 1D). Hereinafter, the configuration of the medical instrument 10 will be described in detail.

The medical instrument 10 is used after placement into a body lumen 70 (see FIGS. 1B to 1D). The first liquid 51 present in the center hole 22 of the main body portion 20 and the second liquid 52 present in the radially outward space 23 of the main body portion 20 are not particularly limited. The first liquid 51 and the second liquid 52 may be of the same type or different types. For example, the first liquid 51 is a drug solution flowing in the center hole 22 and the second liquid 52 is a body fluid such as blood. In the present specification, the first liquid 51 includes a drug solution in which a solid drug fixed on the inner layer side of the peripheral wall portion 21 is dissolved. Likewise, the second liquid 52 includes a drug solution in which a solid drug fixed on the outer layer side of the peripheral wall portion 21 is dissolved.

As illustrated in FIG. 1A, the peripheral wall portion 21 has a two-layered structure divided into the first layer 30 and the second layer 40. In the illustrated example, the first layer 30 constitutes the inner layer and the second layer 40 constitutes the outer layer. The hydrophilic member 33 is disposed on the first layer 30 with the hydrophilic coating 32 applied to the first base portion 31. The hydrophobic member 43 is disposed on the second layer 40 with the hydrophobic coating 42 applied to the second base portion 41. As illustrated in FIGS. 1B and 1C, the first base portion 31 and the second base portion 41 have a wire shape (i.e., a cylindrical shape). In accordance with an exemplary embodiment, the hydrophilic member 33 and the hydrophobic member 43 have a coil shape.

The preferred value of the axial length of the main body portion 20 varies depending on applications and cases such as the position and thickness of the body lumen 70 to be applied. Preferably, the main body portion 20 has an axial length of, for example, 1 mm to 2,000 mm. More specifically, for example, the axial length of the main body portion 20 is 1 mm to 400 mm in the case of application to a stent. The axial length of the main body portion 20 is 300 mm to 2,000 mm in the case of application to a catheter. The preferred value of the outer diameter (thickness) of the main body portion 20 varies depending on cases such as thickness and the position of the body lumen 70 to be applied. Preferably, the main body portion 20 has an outer diameter of, for example, 0.5 mm to 50 mm.

The first base portion 31 and the second base portion 41 materials can include, for example, a metal such as stainless steel (SUS), spring steel, titanium, tungsten, tantalum, and a super-elastic alloy such as a nickel-titanium alloy, hard plastic such as polyimide, polyamide, polyester, polycarbonate, and a glass fiber, and a composite of the materials. The materials of the first base portion 31 and the second base portion 41 may be the same as each other or different from each other.

The shape of the first base portion 31 and the second base portion 41 is not particularly limited. In accordance with an exemplary embodiment, the first base portion 31 and the second base portion 41 can have, for example, a plate shape in addition to the wire shape illustrated in FIGS. 1B and 1C.

In the case of the wire shape, the preferred values of the diameters of the first base portion 31 and the second base portion 41 vary depending on cases such as thickness and the position of the body lumen 70 to be applied and the first base portion 31 and the second base portion 41 preferably have an outer diameter of, for example, 0.01 mm to 0.1 mm. The diameters of the first base portion 31 and the second base portion 41 may or may not be equal to each other.

In the case of the first base portion 31 and the second base portion 41 having a plate shape, it is preferable that the first base portion 31 and the second base portion 41 have a thickness×width of, for example, (0.01 to 0.04) mm×(0.02 to 0.2) mm. The thickness×width of the first base portion 31 and the thickness×width of the second base portion 41 may or may not be equal to each other. In the case of the plate shape, the first base portion 31 or the second base portion 41 can be formed thinner than in the case of the wire shape. The peripheral wall portion 21, which has liquid leakage prevention properties, prevents liquid circulation between the inner layer side and the outer layer side. In accordance with an exemplary embodiment, an "aspect ratio of 1:1 or more" is preferable for improvement of the liquid leakage prevention properties. The aspect ratio is the thickness-to-width ratio of the plate.

The hydrophilic coating 32 material may be any material insofar as the material absorbs water and exhibits swelling properties. The material of the hydrophilic coating 32 can be, for example, a hydrophilic material. Examples of the hydrophilic material include known hydrophilic substances formed of, for example, a cellulose-based polymer substance (such as hydroxypropyl cellulose), a polyethylene oxide-based polymer substance (such as polyethylene glycol), a maleic anhydride-based polymer substance (for example, a maleic anhydride copolymer such as a methyl vinyl ether-maleic anhydride copolymer), an acrylamide-based polymer substance (such as a block copolymer of polyglycidyl methacrylate-dimethyl acrylamide (PGMA-DMAA) and polyacrylamide), water-soluble nylon (registered trademark), polyvinyl alcohol, and polyvinyl pyrrolidone.

The thickness of the hydrophilic coating 32 is not particularly limited. For example, it can be preferable that the hydrophilic coating 32 has a thickness of 0.1 μm to 10 μm in a dry environment (DRY) and has a thickness of 0.5 μm to 50 μm in a wet environment (WET). More specifically, for example, the thickness of the hydrophilic coating 32 is 1 μm to 3 μm in the dry environment (DRY) and 10 μm to 20 μm in the wet environment (WET) in a case where a maleic anhydride-based polymer substance constitutes the hydrophilic coating 32. The thickness of the hydrophilic coating 32 can be, for example, 1 μm to 2 μm in the dry environment (DRY) and 3 μm to 5 μm in the wet environment (WET) in a case where an acrylamide-based polymer substance constitutes the hydrophilic coating 32.

The hydrophobic coating 42 material may be any material insofar as the material exhibits hydrophobicity. The hydrophobic coating 42 material can be, for example, a hydrophobic material. Examples of the hydrophobic material include polytetrafluoroethylene (PTFE), fluorinated ethylene propylene (FEP), reaction-curable silicone, and a substance with low surface free energy terminated with alkyl and perfluoroalkyl groups. In addition, the hydrophobic coating 42 exhibiting hydrophobicity may be configured by plasma irradiation by means of a fluorine-based gas or laser micromachining.

In accordance with an exemplary embodiment, the thickness of the hydrophobic coating 42 can be, for example, 1 μm to 40 μm in a case where, for example, polytetrafluoroethylene (PTFE) constitutes the hydrophobic coating 42.

As illustrated in FIGS. 1B and 1C, the first base portions 31 are disposed at a pitch p1 (i.e., distance between a center point of adjacent first base portions 31) which allows the swollen hydrophilic coatings 32 of the adjacent hydrophilic members 33 to be in contact with each other, which can help prevent the first liquid 51 and the second liquid 52 from circulating through the peripheral wall portion 21 by bringing the adjacent hydrophilic members 33 into contact with each other. In accordance with an exemplary embodiment, the maximum gap (pitch p1) of the lattice of the first base portion 31 can be, for example, approximately two to six times the film thickness in the dry environment (DRY) although the maximum gap depends on the linearity between the film thickness in the dry environment (DRY) and the film thickness in the wet environment (WET). The first base portions 31 may be disposed at the pitch p1 or less and the adjacent hydrophilic members 33 may be in contact with each other in the dry environment (DRY). In this case, the swollen hydrophilic coatings 32 come into contact with each other more strongly in the wet environment (WET).

As illustrated in FIGS. 1B and 1C, the first layer 30 seals the first liquid 51 by the swollen hydrophilic coatings 32 coming into contact with each other. However, the first liquid 51, though minute (or relatively very small) in amount, reaches the space between the first layer 30 and the second layer 40 through the hydrophilic coating 32 itself. Although the second layer 40 is stacked at a position in contact with the second liquid 52, it can be said that the second layer 40 is stacked at a position in contact with the first liquid 51 as described above.

Accordingly, the second base portions 41 are disposed at a pitch p2 (i.e., distance between a center point of adjacent second base portions 41), which sets the space between the hydrophobic coatings 42 of the adjacent hydrophobic members 43 to a dimension smaller than the gap through which the first liquid 51 and the second liquid 52 pass, which can help prevent the first liquid 51 and the second liquid 52 from circulating through the peripheral wall portion 21.

Wettability, capillarity, liquid viscosity, and the like relate to the elements of liquid passage through a minute (or relatively small) gap. Accordingly, the upper limit dimension of the micro gap between the hydrophobic coatings 42 varies with the material constituting the hydrophobic coating 42 and the types of the first liquid 51 and the second liquid 52. Although no specific dimension can be specified as the upper limit dimension of the minute gap, the upper limit dimension, for example, is approximately 0 mm to 1 mm.

In accordance with an exemplary embodiment, as illustrated in FIG. 1C, the first liquid 51 and the second liquid 52 can be prevented from circulating through the peripheral wall portion 21. Starting from this state, the space between the adjacent hydrophilic members 33 and the space between the adjacent hydrophobic members 43 are expanded as illustrated in FIG. 1D. The space between the adjacent hydrophilic members 33 and the space between the adjacent hydrophobic members 43 can be expanded by, for example, inflation of the balloon that is disposed in the center hole 22 of the main body portion 20. As a result, the first liquid 51 and the second liquid 52 circulate again through the peripheral wall portion 21. In this manner, the medical instrument 10 is capable of controlling liquid circulation through the peripheral wall portion 21. Accordingly, it is possible to prevent circulation of the first liquid 51 and the second liquid 52 until the main body portion 20 is positioned in a desired place in the body lumen 70 and it is possible to circulate the first liquid 51 and the second liquid 52 with the main body portion 20 positioned in the desired place.

Figure 2A:
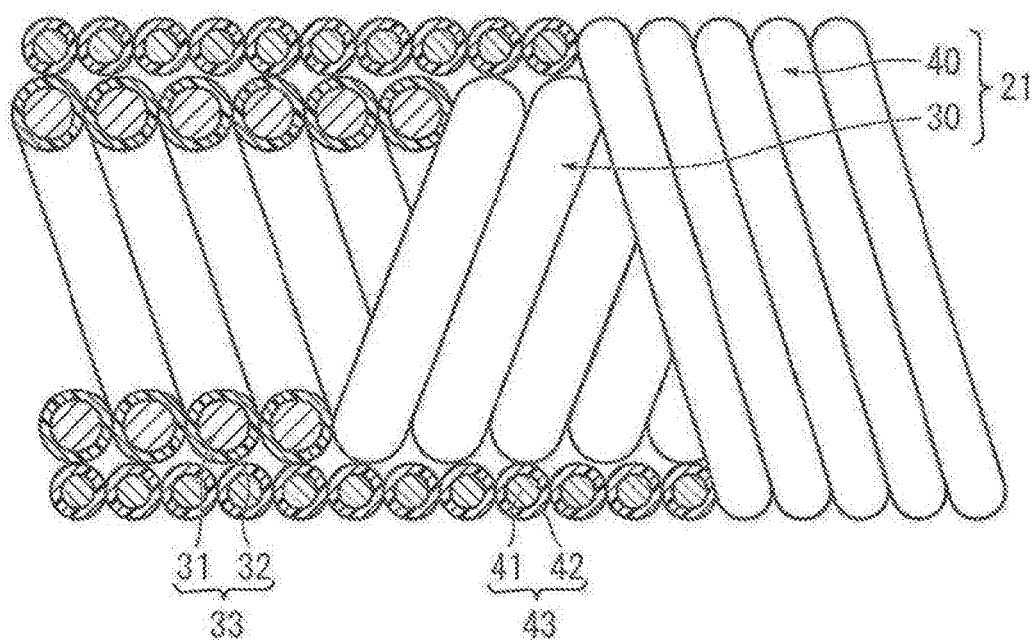
FIG. 2A is a cross-sectional view of a main part illustrating a main body portion in which hydrophilic and hydrophobic members have a coil shape.
Figure 2B:
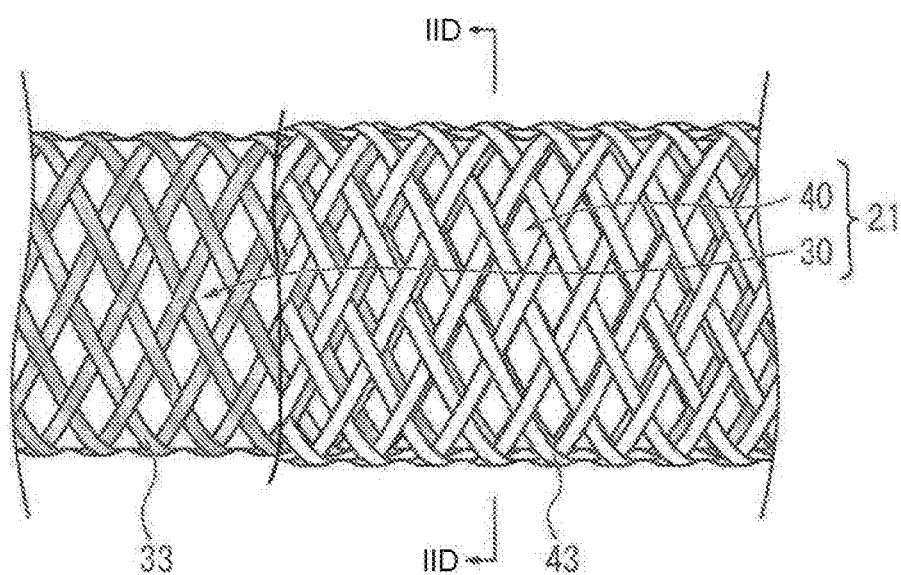
FIG. 2B is a side view illustrating a main body portion in which hydrophilic and hydrophobic members have a mesh shape.
Figure 2C:
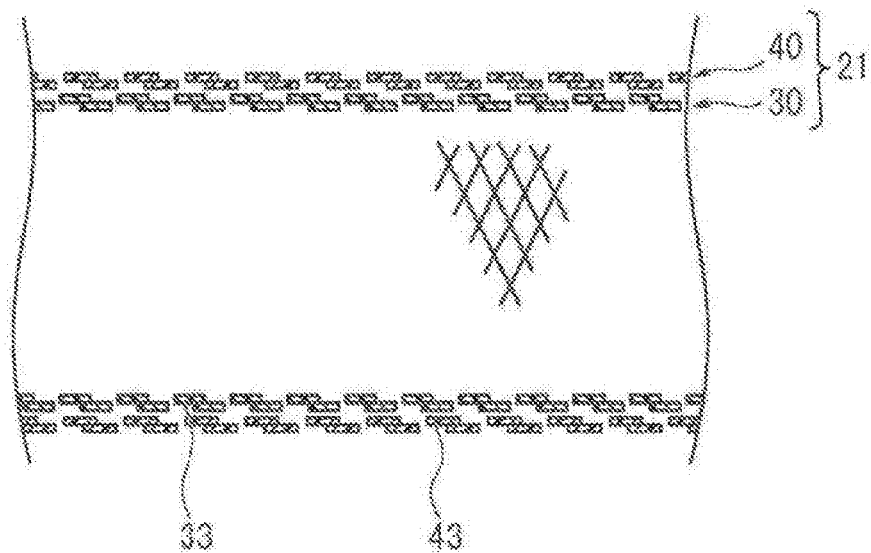
FIG. 2C is a longitudinal cross-sectional view illustrating the mesh shape illustrated in FIG. 2B.
Figure 2D:
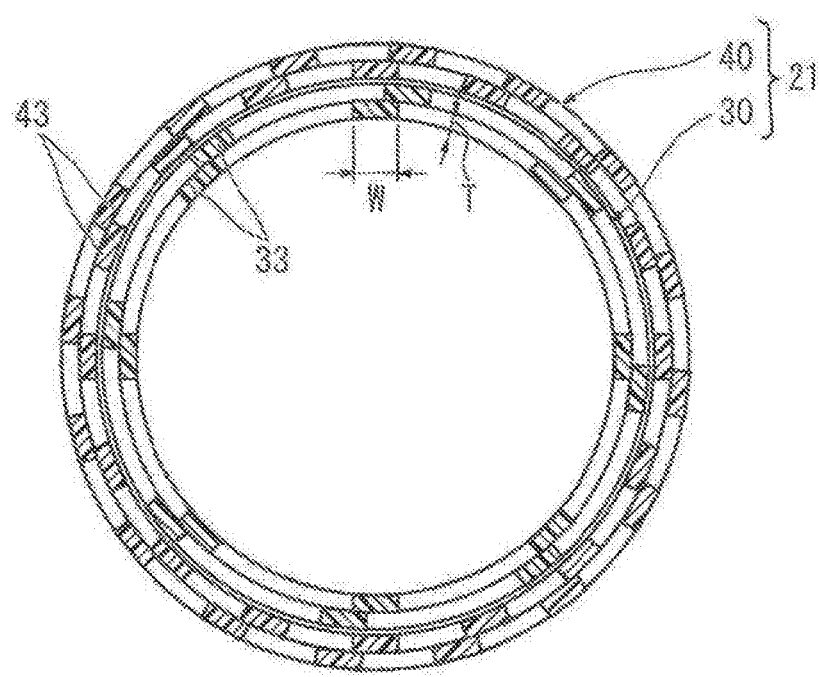
FIG. 2D is a cross-sectional view taken along line IID-IID of FIG. 2B.
Figure 2E:
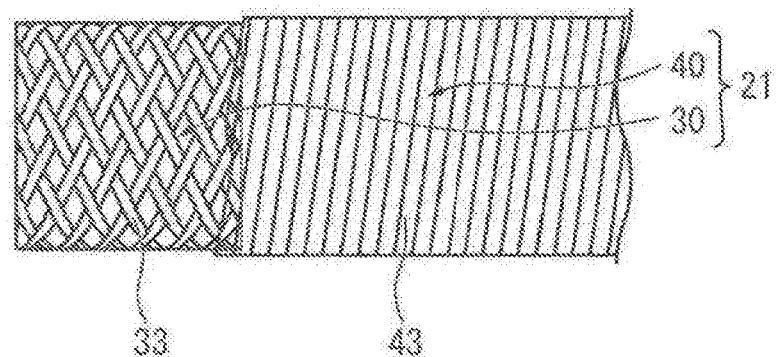
FIG. 2E is a cross-sectional view of a main part illustrating a main body portion in which a mesh-shaped hydrophilic member and a coil-shaped hydrophobic member are stacked.
Figure 2F:
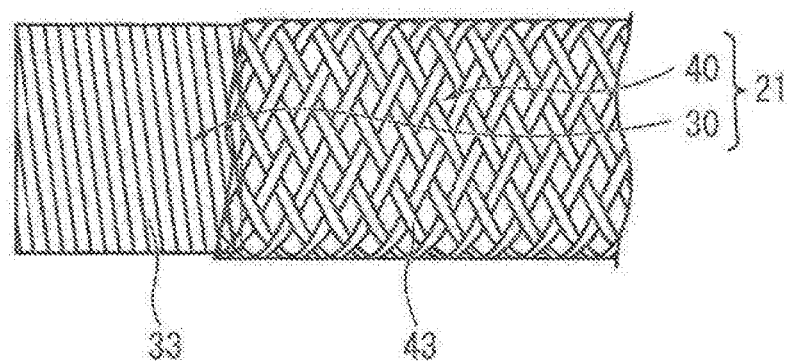
FIG. 2F is a cross-sectional view of a main part illustrating a main body portion in which a coil-shaped hydrophilic member and a mesh-shaped hydrophobic member are stacked.

FIG. 2A is a cross-sectional view of a main part illustrating a main body portion in which hydrophilic and hydrophobic members have a coil shape. FIG. 2B is a side view illustrating a main body portion in which hydrophilic and hydrophobic members have a mesh shape. FIG. 2C is a longitudinal cross-sectional view illustrating the mesh shape illustrated in FIG. 2B. FIG. 2D is a cross-sectional view taken along line IID-IID of FIG. 2B. FIG. 2E is a cross-sectional view of a main part illustrating a main body portion in which a mesh-shaped hydrophilic member and a coil-shaped hydrophobic member are stacked. FIG. 2F is a cross-sectional view of a main part illustrating a main body portion in which a coil-shaped hydrophilic member and a mesh-shaped hydrophobic member are stacked.

The gap parts illustrated in FIGS. 2B to 2F are exaggerated in size so that grasping of the mesh shape is facilitated. As described above, the first base portions 31 are disposed at the pitch p1 and the second base portions 41 are disposed at the pitch p2.

The shape of the first base portion 31 is not particularly limited. The first base portion 31 has, for example, a wire shape or a plate shape. Likewise, the shape of the second base portion 41 is not particularly limited and the second base portion 41 has, for example, a wire shape or a plate shape. The shape of the hydrophilic member 33 is not particularly limited. The hydrophilic member 33 has, for example, a coil shape, a ring shape, or a mesh shape. Likewise, the shape of the hydrophobic member 43 is not particularly limited and the hydrophobic member 43 has, for example, a coil shape, a ring shape, or a mesh shape. Both the hydrophilic member 33 and the hydrophobic member 43, for example, do not have to have a coil shape. Both the hydrophilic member 33 and the hydrophobic member 43, for example, do not have to have a mesh shape.

More specifically, the first base portion 31 and the second base portion 41 can have a wire shape as illustrated in FIG. 2A. The hydrophilic member 33 and the hydrophobic member 43 are formed in a coil shape. In accordance with an exemplary embodiment, the peripheral wall portion 21 is a two-layered structure. In accordance with an exemplary embodiment, the hydrophilic first layer 30 and the hydrophobic second layer 40 can be sequentially stacked from the inner layer toward the outer layer.

As illustrated in FIG. 2D, the first base portion 31 and the second base portion 41 have a plate shape. Reference sign T indicates the thickness of the plate. Reference sign W indicates the width of the plate. As illustrated in FIGS. 2B and 2C, the hydrophilic member 33 and the hydrophobic member 43 are formed in a mesh shape. In accordance with an exemplary embodiment, the mesh shape (braided structure) can be formed by braiding of a plurality of the hydrophilic members 33 and a plurality of the hydrophobic members 43. As in FIG. 2A, the peripheral wall portion 21 is a two-layered structure and the hydrophilic first layer 30 and the hydrophobic second layer 40 are sequentially stacked from the inner layer toward the outer layer. In the illustrated example, the hydrophilic members 33 are braided and become the mesh-shaped hydrophilic first layer 30. The hydrophobic members 43 are braided on the hydrophilic first layer 30 and become the mesh-shaped hydrophobic second layer 40.

As illustrated in FIG. 2E, the hydrophilic member 33 is formed in a mesh shape and the hydrophobic member 43 is formed in a coil shape. As in FIG. 2A, the peripheral wall portion 21 is a two-layered structure and the hydrophilic first layer 30 and the hydrophobic second layer 40 are sequentially stacked from the inner layer toward the outer layer.

As illustrated in FIG. 2F, the hydrophilic member 33 is formed in a coil shape and the hydrophobic member 43 is formed in a mesh shape. As in FIG. 2A, the peripheral wall portion 21 is a two-layered structure and the hydrophilic first layer 30 and the hydrophobic second layer 40 are sequentially stacked from the inner layer toward the outer layer.

Although one wire constitutes the first base portion 31 and the second base portion 41 in FIG. 2A, a wire bundle in which a plurality of wires are bundled may constitute the first base portion 31 and the second base portion 41. In accordance with an exemplary embodiment, the main body portion 20 may be configured by bundling of the hydrophilic members 33 and the hydrophobic members 43 that are formed in a ring shape and arranged in an axial direction.

Although the peripheral wall portion 21 needs to include at least one hydrophilic first layer 30 and at least one hydrophobic second layer 40, an appropriate selection can be made as to whether the innermost layer of the peripheral wall portion 21 will be the hydrophilic first layer 30 or the hydrophobic second layer 40. In a case where another member is inserted through the center hole 22, for example, it can be preferable to use the hydrophilic first layer 30 as the innermost layer in order to enhance slidability with respect to the member. The slidability of the hydrophilic first layer 30 with respect to the member is enhanced by the inside of the center hole 22 being primed and wetted with a saline solution or the like. The hydrophilic first layer 30 may be used as the innermost layer in a case where it is desired to swell the innermost layer. In accordance with an exemplary embodiment, for liquid circulation through the center hole 22, the hydrophobic second layer 40 can be used as the innermost layer.

In accordance with an exemplary embodiment, an appropriate selection can be made as to whether the outermost layer of the peripheral wall portion 21 will be the hydrophilic first layer 30 or the hydrophobic second layer 40. In a case where the main body portion 20 of the medical instrument 10 is placed into the body lumen 70, for example, the hydrophobic second layer 40 is preferably used as the outermost layer so that no deviation is likely to occur with respect to the inner surface of the body lumen 70. In a case where the main body portion 20 of the medical instrument 10 moves in the body lumen 70, the slidability of the medical instrument 10 with respect to the inner surface of the body lumen 70 should be enhanced, and thus the hydrophilic first layer 30 is more preferable than the hydrophobic second layer 40 as the outermost layer. In accordance with an exemplary embodiment, the hydrophilic first layer 30 may be used as the outermost layer in a case where it is desired to swell the outermost layer.

Figure 3A:
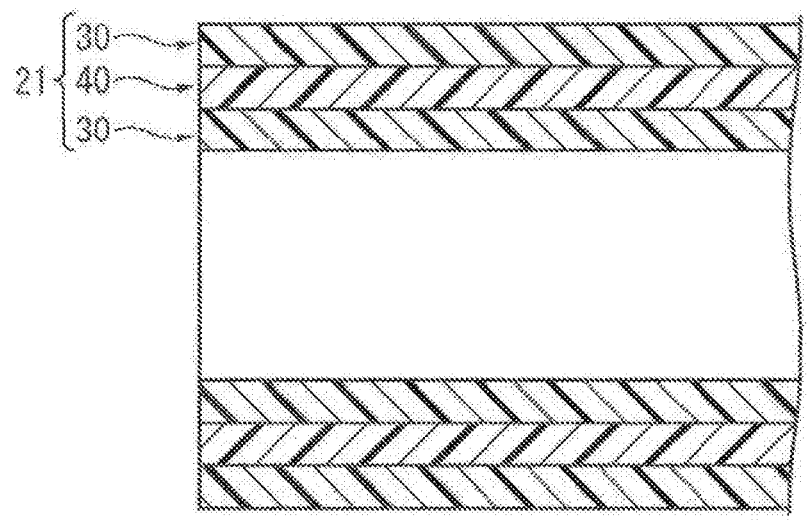
FIG. 3A is a cross-sectional view schematically illustrating a main body portion in which a hydrophilic member, a hydrophobic member, and a hydrophilic member are sequentially stacked from an inner layer side toward an outer layer side.
Figure 3B:
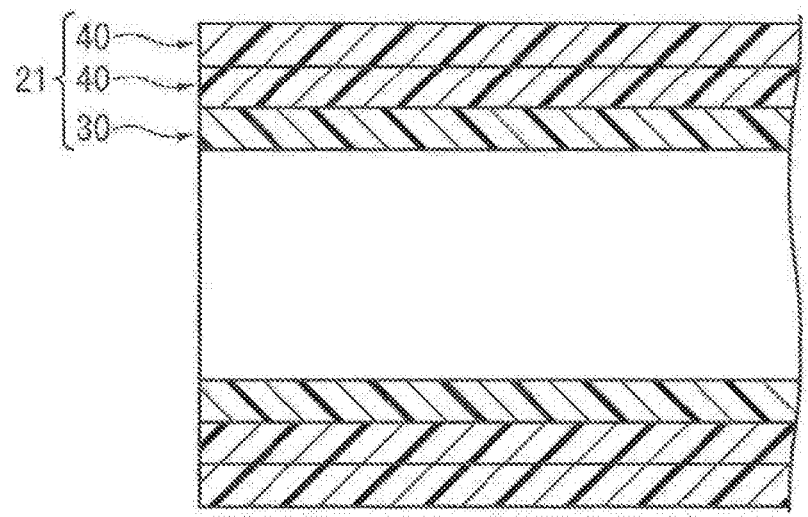
FIG. 3B is a cross-sectional view schematically illustrating a main body portion in which a hydrophilic member, a hydrophobic member, and a hydrophobic member are sequentially stacked from the inner layer side toward the outer layer side.
Figure 3C:
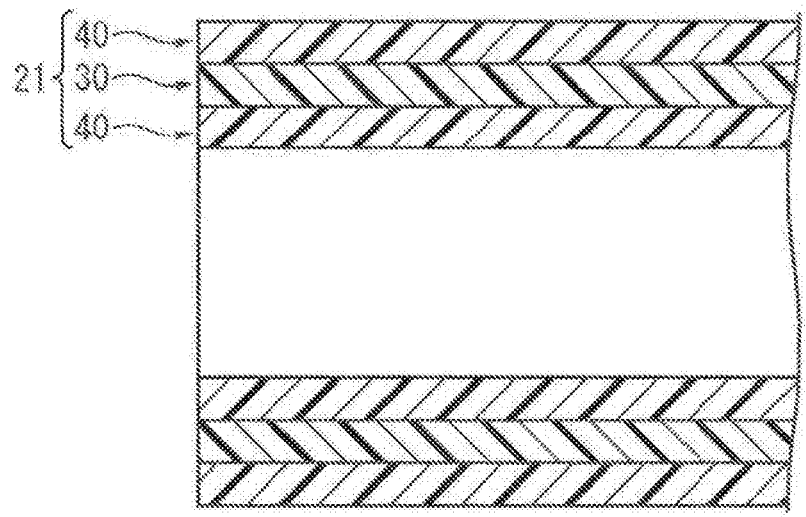
FIG. 3C is a cross-sectional view schematically illustrating a main body portion in which a hydrophobic member, a hydrophilic member, and a hydrophobic member are sequentially stacked from the inner layer side toward the outer layer side.
Figure 3D:
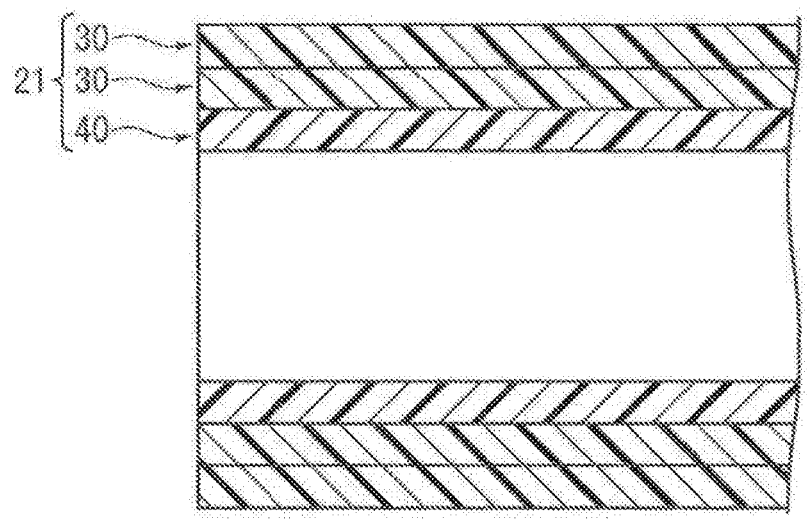
FIG. 3D is a cross-sectional view schematically illustrating a main body portion in which a hydrophobic member, a hydrophilic member, and a hydrophilic member are sequentially stacked from the inner layer side toward the outer layer side.

FIG. 3A is a cross-sectional view schematically illustrating a main body portion in which a hydrophilic member, a hydrophobic member, and a hydrophilic member are sequentially stacked from the inner layer side toward the outer layer side. FIG. 3B is a cross-sectional view schematically illustrating a main body portion in which a hydrophilic member, a hydrophobic member, and a hydrophobic member are sequentially stacked from the inner layer side toward the outer layer side. FIG. 3C is a cross-sectional view schematically illustrating a main body portion in which a hydrophobic member, a hydrophilic member, and a hydrophobic member are sequentially stacked from the inner layer side toward the outer layer side. FIG. 3D is a cross-sectional view schematically illustrating a main body portion in which a hydrophobic member, a hydrophilic member, and a hydrophilic member are sequentially stacked from the inner layer side toward the outer layer side.

FIGS. 3A to 3D are schematic diagrams illustrating exemplary stacked structures. The first base portion 31 and the second base portion 41 may have any of the wire shape and the plate shape described above. The hydrophilic member 33 and the hydrophobic member 43 may have any of a coil shape, a ring shape, and a mesh shape.

The peripheral wall portion 21 is not limited to the two-layered structures illustrated in FIGS. 2A to 2F. In accordance with an exemplary embodiment, although the peripheral wall portion 21 needs to include at least one hydrophilic first layer 30 and at least one hydrophobic second layer 40, the hydrophilic first layer 30 or the hydrophobic second layer 40 can be further stacked for three or more layers to be formed.

In accordance with an exemplary embodiment, the peripheral wall portion 21 is a three-layered structure as illustrated in FIG. 3A and the hydrophilic first layer 30, the hydrophobic second layer 40, and the hydrophilic first layer 30 are sequentially stacked from the inner layer toward the outer layer.

As illustrated in FIG. 3B, the peripheral wall portion 21 is a three-layered structure as in FIG. 3A and the hydrophilic first layer 30, the hydrophobic second layer 40, and the hydrophobic second layer 40 are sequentially stacked from the inner layer toward the outer layer.

As illustrated in FIG. 3C, the peripheral wall portion 21 is a three-layered structure as in FIG. 3A and the hydrophobic second layer 40, the hydrophilic first layer 30, and the hydrophobic second layer 40 are sequentially stacked from the inner layer toward the outer layer.

As illustrated in FIG. 3D, the peripheral wall portion 21 is a three-layered structure as in FIG. 3A and the hydrophobic second layer 40, the hydrophilic first layer 30, and the hydrophilic first layer 30 are sequentially stacked from the inner layer toward the outer layer.

Test Example

Figure 4A:
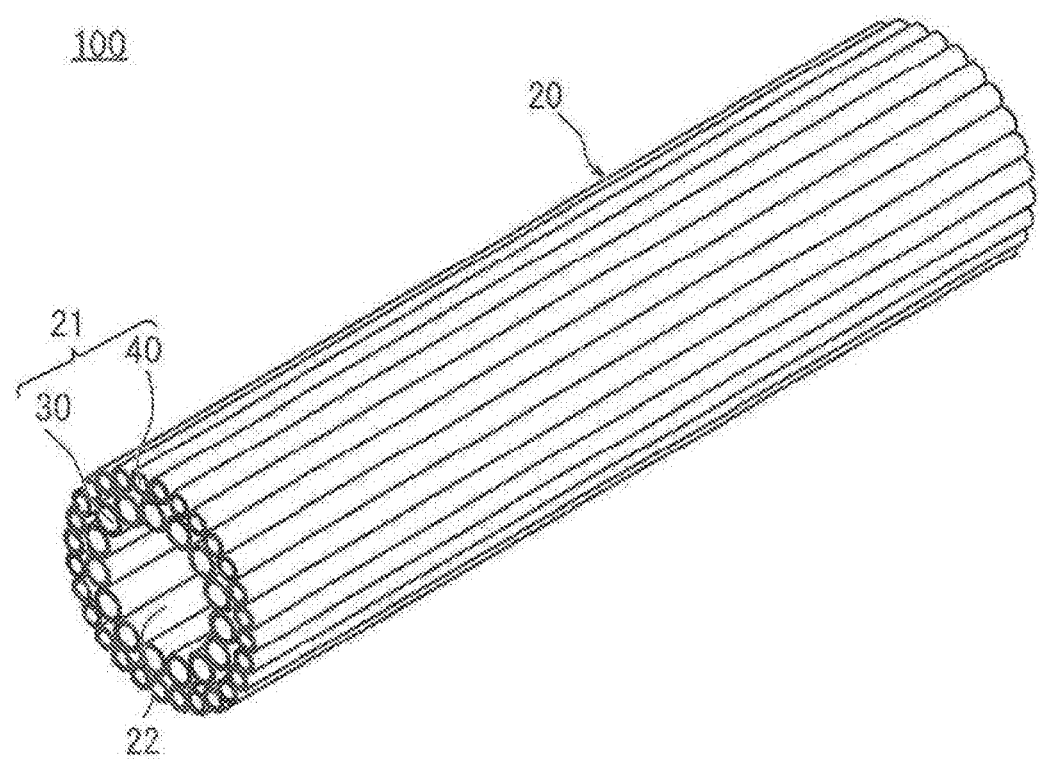
FIG. 4A is a perspective view illustrating a sample corresponding to the main body portion of the medical instrument.
Figure 4B:
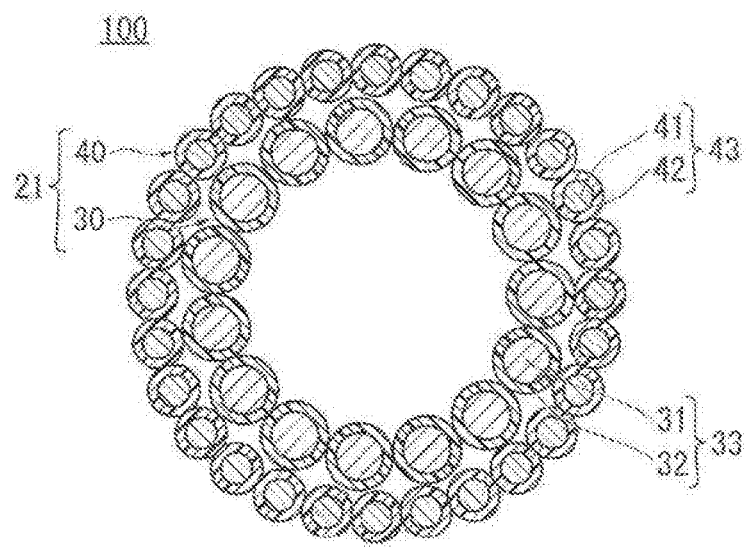
FIG. 4B is a lateral cross-sectional view illustrating the sample in which the inner layer of a peripheral wall portion is a hydrophilic first layer and the outer layer of the peripheral wall portion is a hydrophobic second layer.
Figure 4C:
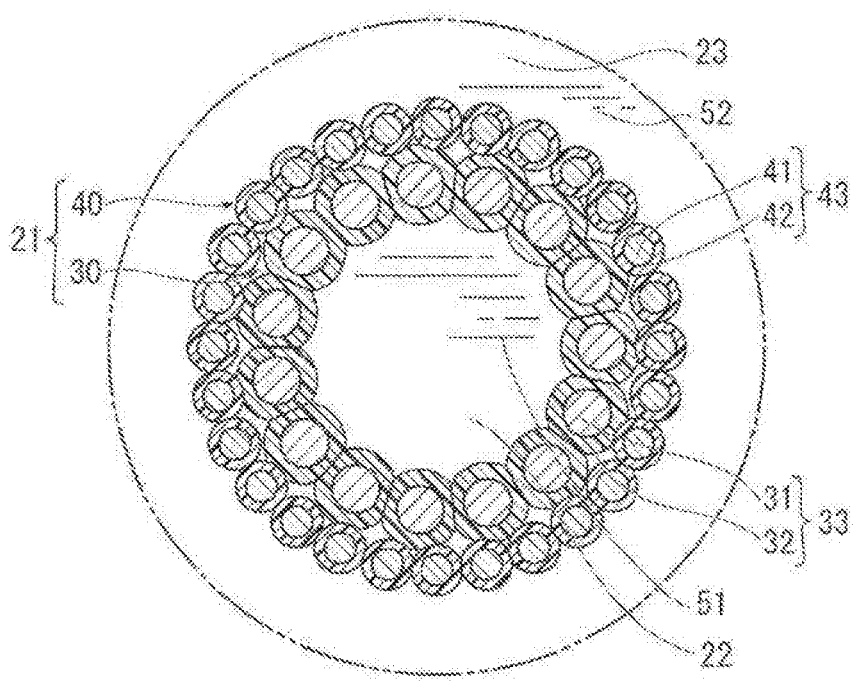
FIG. 4C is a lateral cross-sectional view illustrating a state where a liquid leakage test is performed on the peripheral wall portion by means of the sample illustrated in FIG. 4B.
Figure 4D:
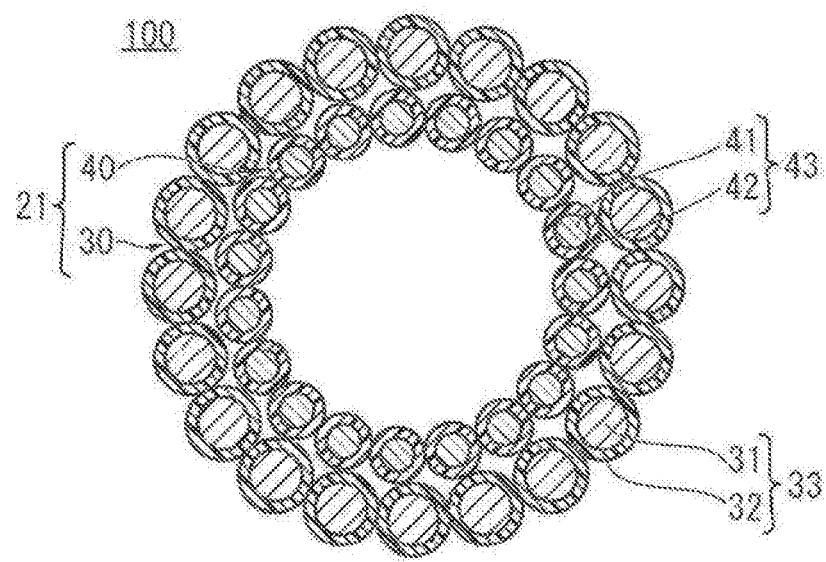
FIG. 4D is a lateral cross-sectional view illustrating the sample in which the inner layer of the peripheral wall portion is the hydrophobic second layer and the outer layer of the peripheral wall portion is the hydrophilic first layer.
Figure 4E:
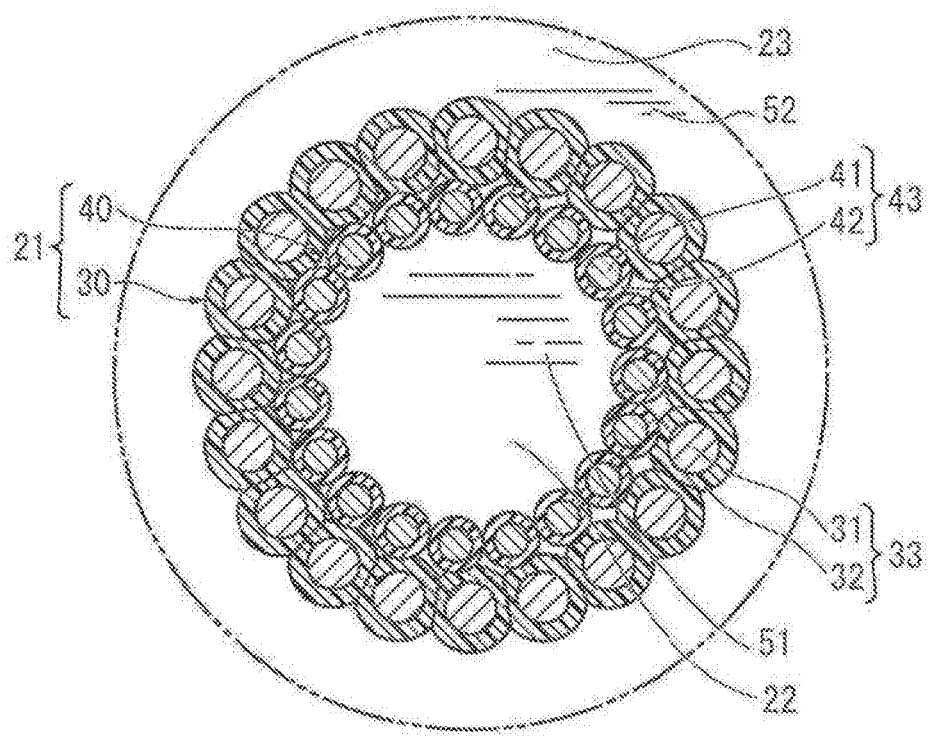
FIG. 4E is a lateral cross-sectional view illustrating a state where a liquid leakage test is performed on the peripheral wall portion by means of the sample illustrated in FIG. 4D.
Figure 4F:
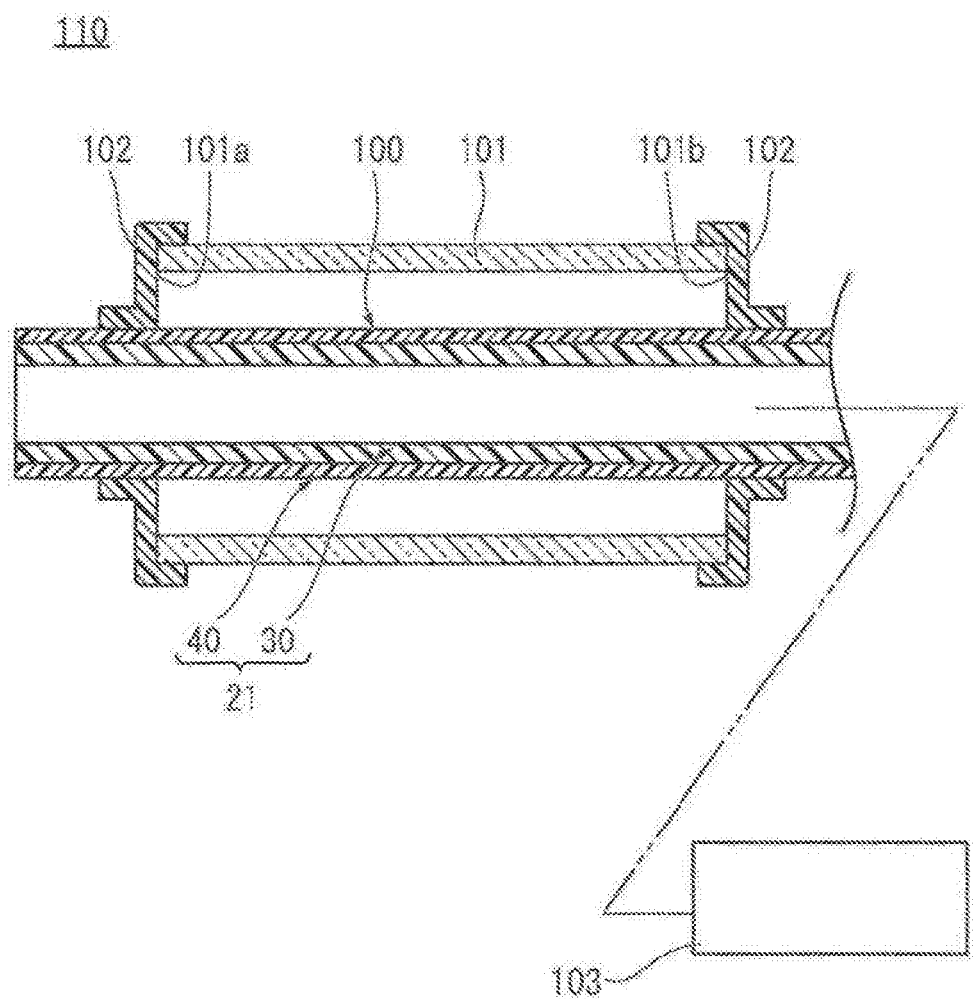
FIG. 4F is a cross-sectional view illustrating a main part of an experimental device that conducted a test as to whether the peripheral wall portion prevents circulation of a first liquid and a second liquid.

FIG. 4A is a perspective view illustrating a sample 100 corresponding to the main body portion 20 of the medical instrument 10. FIG. 4B is a lateral cross-sectional view illustrating the sample 100 in which the inner layer of the peripheral wall portion 21 is the hydrophilic first layer 30 and the outer layer of the peripheral wall portion 21 is the hydrophobic second layer 40. FIG. 4C is a lateral cross-sectional view illustrating a state where a liquid leakage test is performed on the peripheral wall portion 21 by means of the sample 100 illustrated in FIG. 4B. FIG. 4D is a lateral cross-sectional view illustrating the sample 100 in which the inner layer of the peripheral wall portion 21 is the hydrophobic second layer 40 and the outer layer of the peripheral wall portion 21 is the hydrophilic first layer 30. FIG. 4E is a lateral cross-sectional view illustrating a state where a liquid leakage test is performed on the peripheral wall portion 21 by means of the sample 100 illustrated in FIG. 4D. FIG. 4F is a cross-sectional view illustrating a main part of an experimental device 110 that conducted a test as to whether the peripheral wall portion 21 prevents circulation of the first liquid 51 and the second liquid 52.

A plurality of the samples 100 imitating the main body portion 20 were prepared and the test was conducted as to whether the peripheral wall portion 21 helps prevent circulation of the first liquid 51 and the second liquid 52.

The prepared samples 100 were divided into six types.
Sample #1: Inner layer of peripheral wall portion 21 hydrophilic first layer 30
Outer layer of peripheral wall portion 21 hydrophobic second layer 40
Sample #2: Inner layer of peripheral wall portion 21 hydrophobic second layer 40
Outer layer of peripheral wall portion 21 hydrophilic first layer 30
Sample #3: Inner layer of peripheral wall portion 21 hydrophilic first layer 30
Outer layer of peripheral wall portion 21 hydrophilic first layer 30
Sample #4: Inner layer of peripheral wall portion 21 hydrophobic second layer 40
Outer layer of peripheral wall portion 21 hydrophobic second layer 40
Sample #5: Inner layer of peripheral wall portion 21 metal-hydrophilized wire
Outer layer of peripheral wall portion 21 hydrophobic second layer 40
Sample #6: Inner layer of peripheral wall portion 21 hydrophobic second layer 40
Outer layer of peripheral wall portion 21 metal-hydrophilized wire A pipe as a core bar (diameter: 1.77 mm), a double-sided tape for disposing and fixing a wire around the core bar, a seal tape for preventing water leakage from an end portion, a hydrophilic coated wire, and a hydrophobic coated wire were prepared first for the sample 100 to be created. A guide wire (diameter: 0.46 mm) cut to 10 cm to 12 cm was used as the hydrophilic coated wire. A hydrophilic coating formed of a maleic anhydride-based polymer substance (methyl vinyl ether-maleic anhydride copolymer) was used as the hydrophilic coating 32. A PTFE-coated wire (diameter: 0.35 mm) cut to 10 cm to 12 cm was used as the hydrophobic coated wire. Regarding Samples #5 and #6, a metal-hydrophilized wire was used by irradiation of a metal wire with plasma.

Sample #1 was created by the following procedure. First, the hydrophilic coated wire is arranged in a planar shape on a flat surface and the double-sided tape is affixed to both ends of the wire. The hydrophilic coated wire held by the tape is wound around the surface of the core bar, and then the inner layer (hydrophilic first layer 30) is formed. Next, the hydrophobic coated wire is arranged in a planar shape on a flat surface and the double-sided tape is affixed to both ends of the wire. The core bar around which the inner layer is wound is put on the hydrophobic coated wire held by the tape. The hydrophobic coated wire is wound on the inner layer, and then the outer layer (hydrophobic second layer 40) is formed. Subsequently, the core bar was carefully pulled out and Sample #1 was completed. The part where the core bar was pulled out corresponds to the center hole 22 of the main body portion 20. Samples #2 to #6 were created in the same manner.

In Sample #1, 15 hydrophilic coated wires form the inner layer of the peripheral wall portion 21 and 28 hydrophobic coated wires form the outer layer of the peripheral wall portion 21 as illustrated in FIGS. 4A and 4B. In Sample #2, 19 hydrophobic coated wires form the inner layer of the peripheral wall portion 21 and 20 hydrophilic coated wires form the outer layer of the peripheral wall portion 21 as illustrated in FIG. 4D.

As illustrated in FIG. 4F, the experimental device 110 simulated a state where the main body portion 20 is placed in the body lumen 70 in order to conduct the test as to whether the peripheral wall portion 21 helps prevent circulation of the first liquid 51 and the second liquid 52. First, the sample 100 imitating the main body portion 20 is inserted through a transparent tube 101 imitating the body lumen 70. The space between the sample 100 and one end portion 101a of the transparent tube 101 is sealed by a seal tape 102. The other end portion 101b of the transparent tube 101 is directed upward and water is injected into the transparent tube 101 by means of a pipette tube. After the transparent tube 101 is filled with the water, the space between the sample 100 and the other end portion 101b of the transparent tube 101 is sealed by the seal tape 102. The distal end of a syringe 103 containing water stained with red ink is inserted into one open end of the inner layer of the sample 100. Subsequently, the stained water was injected from the syringe 103 into the inner layer of the sample 100. As for Sample #1, a change in the color of the water in the transparent tube 101 was observed as illustrated in FIG. 4C. As for Sample #2, a change in the color of the water in the transparent tube 101 was observed as illustrated in FIG. 4E. Likewise, a change in the color of the water in the transparent tube 101 was observed in Samples #3 to #6.

The result of the observation is as follows.

Sample #1 (inner layer: hydrophilic, outer layer: hydrophobic): color of water in transparent tube 101 not changed.

Sample #2 (inner layer: hydrophobic, outer layer: hydrophilic): color of water in transparent tube 101 not changed.

Sample #3 (inner layer: hydrophilic, outer layer: hydrophilic): color of water in transparent tube 101 changed.

Sample #4 (inner layer: hydrophobic, outer layer: hydrophobic): color of water in transparent tube 101 changed.

Sample #5 (inner layer: metal-hydrophilized, outer layer: hydrophobic): color of water in transparent tube 101 changed.

Sample #6 (inner layer: hydrophobic, outer layer: metal-hydrophilized): color of water in transparent tube 101 changed.

As in Sample #1 (inner layer: hydrophilic, outer layer: hydrophobic) and Sample #2 (inner layer: hydrophobic, outer layer: hydrophilic), liquid leakage through the peripheral wall portion 21 did not occur in the case of lamination of the hydrophilic first layer 30 and the hydrophobic second layer 40.

As in Sample #3 (inner layer: hydrophilic, outer layer: hydrophilic) and Sample #4 (inner layer: hydrophobic, outer layer: hydrophobic), liquid leakage through the peripheral wall portion 21 occurred in the case of non-lamination of the hydrophilic first layer 30 and the hydrophobic second layer 40.

As in Sample #5 (inner layer: metal-hydrophilized, outer layer: hydrophobic) and Sample #6 (inner layer: hydrophobic, outer layer: metal-hydrophilized), liquid leakage through the peripheral wall portion 21 occurred in the metal-hydrophilized wire despite lamination of the hydrophilic layer and the hydrophobic second layer 40.

From the result of the experiment, it has been found that the liquid (stained water) in the center hole 22 and the liquid (water) present in the radially outward space 23 can be prevented from circulating through the peripheral wall portion 21 by the adjacent hydrophilic coated wires coming into contact with each other as a result of swelling of the hydrophilic coating 32 in the peripheral wall portion 21, which includes the first layer 30 having the hydrophilic coated wire including a metal wire coated with the hydrophilic coating 32; and the second layer 40 having the hydrophobic coated wire including a metal wire coated with the hydrophobic coating 42, in which the first layer 30 and the second layer 40 are stacked along the radial direction.

Liquid leakage occurred in Sample #3. It is conceivable that the liquid (stained water) in the center hole 22 circulated to the liquid (water) present in the radially outward space 23 through the hydrophilic coating 32 itself, even in the case of lamination of the hydrophilic first layer 30 in two layers, with the limit of the amount of water retention by the hydrophilic coating 32 exceeded. Accordingly, it is conceivable that it can be necessary to provide the hydrophobic second layer 40 sealing the liquid (stained water) in the center hole 22 as in Samples #1 and #2.

Liquid leakage occurred in Sample #4. A shortage (or lack) of sealability is conceivable as the contact between the hydrophilic coated wires that results from swelling of the hydrophilic coating 32 does not occur even with the hydrophobic second layer 40 stacked in two layers.

As described above, the medical instrument 10 has the main body portion 20, in which the center hole 22 and the radially outward space 23 are partitioned by the tubular peripheral wall portion 21. The peripheral wall portion 21 includes at least the first layer 30 on which the hydrophilic member 33, in which the hydrophilic coating 32 is formed on the first base portion 31, is disposed and the second layer 40 on which the hydrophobic member 43, in which the hydrophobic coating 42 is formed on the second base portion 41, is disposed. The peripheral wall portion 21 includes the first layer 30 and the second layer 40 stacked along the radial direction.

In the medical instrument 10 configured as described above, the adjacent hydrophilic members 33 come into contact with each other as a result of swelling of the hydrophilic coating 32, so that the first liquid 51 in the center hole 22 and the second liquid 52 present in the radially outward space 23 can be prevented from circulating through the peripheral wall portion 21.

In accordance with an exemplary embodiment, the first base portions 31 are disposed at the pitch p1, which allows the swollen hydrophilic coatings 32 of the adjacent hydrophilic members 33 to be in contact with each other.

With this configuration, it is possible to prevent the first liquid 51 and the second liquid 52 from circulating through the peripheral wall portion 21 by bringing the adjacent hydrophilic members 33 into contact with each other.

The second base portions 41 are disposed at the pitch p2, which sets the space between the hydrophobic coatings 42 of the adjacent hydrophobic members 43 to a dimension smaller than the gap through which the first liquid 51 and the second liquid 52 pass.

With this configuration, it is possible to prevent the first liquid 51 and the second liquid 52 from passing between the hydrophobic coatings 42 of the adjacent hydrophobic members 43.

In accordance with an exemplary embodiment, the first base portion 31 and the second base portion 41 have a wire shape or a plate shape.

With this configuration, application can be performed to the medical instrument 10 that has a shape suitable for sites to which the main body portion 20 is applied, which include the body lumen 70.

In accordance with an exemplary embodiment, the hydrophilic member 33 and the hydrophobic member 43 can have a coil shape, a ring shape, or a mesh shape.

With this configuration, application can be performed to the medical instrument 10 that has a shape suitable for sites to which the main body portion 20 is applied, which include the body lumen 70.

Next, specific application examples regarding the main body portion 20 will be described. In the following description, "proximal side" refers to the side that is positioned on the side opposite to "distal side" in a case where the side that is introduced into a living body is referred to as "distal side". In addition, the distal portion means a part that includes a certain range in the axial direction from the distal end (most distal end) and the proximal portion means a part that includes a certain range in the axial direction from the proximal end (most proximal end).

Example of Application of Main Body Portion 20 to Catheter 200

Figure 5:
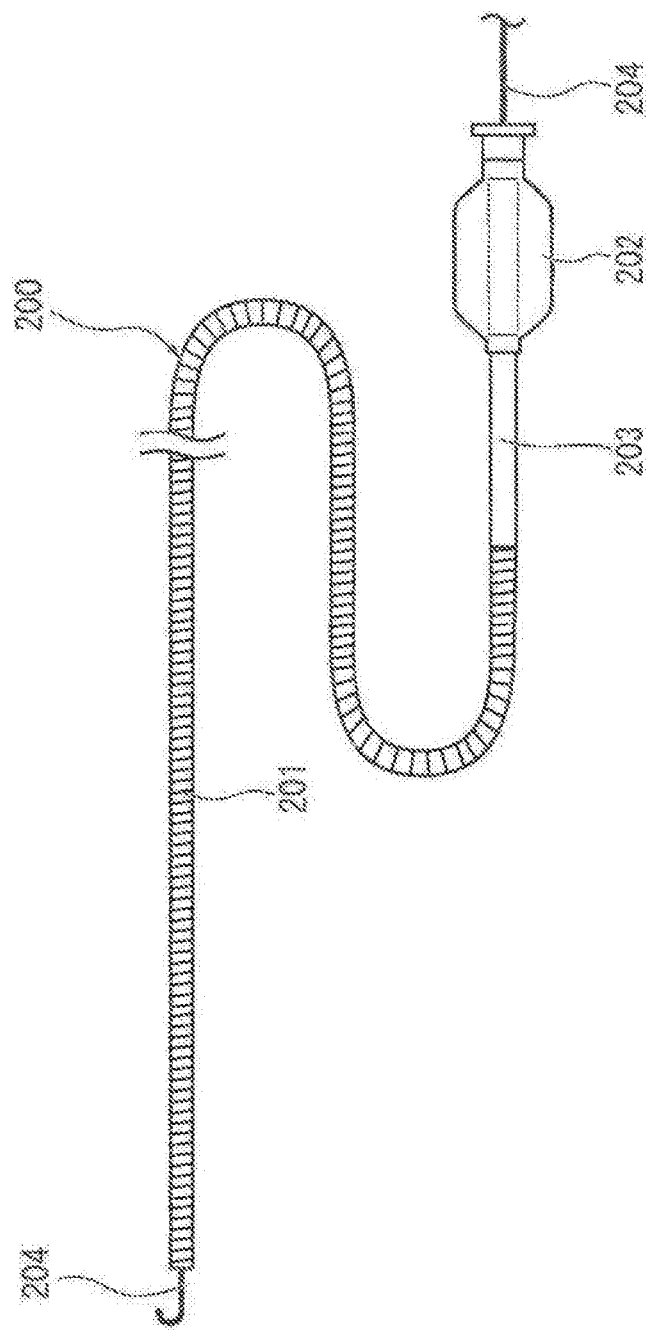
FIG. 5 is a diagram illustrating an example in which the main body portion is applied to a shaft portion of a catheter.

FIG. 5 is a diagram illustrating an example in which the main body portion 20 is applied to a shaft portion 201 of a catheter 200.

Catheters such as microcatheters and guiding catheters are used for diagnosis and treatment in body lumens. Catheters can be used for small-diameter peripheral regions and intricately bent blood vessels, and thus peripheral accessibility (dimensional reduction in diameter), flexibility, and torque transmission performance are required.

In an existing catheter, a composite of a metal reinforcement body layer and a resin-coated layer constitutes a wall portion. The metal reinforcement body layer provides torque transmission performance and lumen retention properties. The resin-coated layer helps prevent liquid circulation between the inner layer side and the outer layer side of the catheter. Accordingly, problems arise from an increase in thickness attributable to resin coating and a decline in torque transmission performance attributable to viscoelastic characteristics unique to resin.

In accordance with an exemplary embodiment, the main body portion 20 described above is suitable for constituting the shaft portion 201 of the catheter 200.

As illustrated in FIG. 5, the catheter 200 has an elongated shaft portion 201, which has a substantially circular cross section and can be introduced into a living body, and a catheter hub 202 connected to the proximal portion of the shaft portion 201. In accordance with an exemplary embodiment, the catheter 200 has an anti-kink protector (strain relief) 203 near the interlock portion between the shaft portion 201 and the catheter hub 202. The catheter 200 may not be provided with the anti-kink protector 203. A guide wire 204 can be inserted through the lumen of the shaft portion 201.

The shaft portion 201 is a flexible tubular member in which an axially extending lumen is formed. In accordance with an exemplary embodiment, the preferred value of the length of the shaft portion 201 varies depending on cases such as thickness and the position of a blood vessel to be applied. The length of the shaft portion 201 can be, for example, approximately 500 mm to 2,000 mm. Preferably, the length of the shaft portion 201 can be, for example, approximately 500 mm to 1,500 mm. The preferred value of the outer diameter (thickness) of the shaft portion 201 varies depending on cases such as thickness and the position of a blood vessel to be applied. The outer diameter of the shaft portion 201 can be, for example, approximately 0.4 mm to 5.0 mm. Preferably, the outer diameter of the shaft portion 201 can be, for example, approximately 0.5 mm to 3.0 mm.

The preferred value of the inner diameter of the shaft portion 201 varies depending on cases such as thickness and the position of a blood vessel to be applied. The inner diameter of the shaft portion 201 can be, for example, approximately 0.3 mm to 4.0 mm. Preferably, the inner diameter of the shaft portion 201 can be, for example, approximately 0.4 mm to 2.0 mm.

In accordance with an exemplary embodiment, the first base portion 31 and the second base portion 41 of the shaft portion 201 of the catheter 200 have a wire shape as illustrated in FIG. 2A. The hydrophilic member 33 and the hydrophobic member 43 can be formed in a coil shape.

In accordance with an exemplary embodiment, the first base portion 31 and the second base portion 41 may have a plate shape as illustrated in FIGS. 2B to 2D. The hydrophilic member 33 and the hydrophobic member 43 may be formed in a mesh shape.

In accordance with an exemplary embodiment, the hydrophilic member 33 that has a mesh shape and the hydrophobic member 43 that has a coil shape may be stacked in the shaft portion 201 as illustrated in FIG. 2E. The hydrophilic member 33 that has a coil shape and the hydrophobic member 43 that has a mesh shape may be stacked in the shaft portion 201 as illustrated in FIG. 2F.

As illustrated in FIGS. 2A to 2F, the peripheral wall portion 21 is a structure that has at least two layers. The hydrophilic first layer 30 and the hydrophobic second layer 40 are sequentially stacked from the inner layer toward the outer layer. As for the hydrophilic first layer 30, the adjacent hydrophilic members 33 come into contact with each other as a result of swelling of the hydrophilic coating 32 caused by water, a body fluid, a drug solution, or the like. As a result, the peripheral wall portion 21 helps prevent liquid circulation between the inner layer side and the outer layer side. The hydrophobic second layer 40 blocks inflow of blood outside the catheter 200 to the inner layer side.

In accordance with an exemplary embodiment, the peripheral wall portion 21 can be a three-layered structure in which the hydrophilic first layer 30, the hydrophobic second layer 40, and the hydrophilic first layer 30 are sequentially stacked from the inner layer toward the outer layer as illustrated in FIG. 3A. Considering an actual use of the catheter 200, the hydrophilic first layer 30 is more preferable than the hydrophobic second layer 40 as the outermost layer, which enhances slidability with respect to the inner surface of the body lumen 70 in that the catheter 200 is the medical instrument 10 that moves in the body lumen 70.

In accordance with an exemplary embodiment, the layered structure of the catheter 200 may not be constant from the proximal portion to the distal portion. For example, the hydrophilic first layer 30, the hydrophobic second layer 40, and the hydrophilic first layer 30 may be sequentially stacked from the inner layer toward the outer layer on the distal side (stacked structure in FIG. 3A) with the hydrophobic second layer 40, the hydrophilic first layer 30, and the hydrophobic second layer 40 sequentially stacked from the inner layer toward the outer layer on the proximal side (stacked structure in FIG. 3C).

In accordance with an exemplary embodiment, a resin-coated layer (i.e., an inner layer plus (+) an outer layer) and a reinforcement body layer form a stacked structure constituting a catheter wall portion of an existing catheter. The resin-coated layer is to prevent liquid circulation between inside and outside layers of a shaft portion. The reinforcement body layer is formed by coil winding of a metal wire ($\varphi 0.04$ mm (i.e., an outer diameter of 0.04 mm)) on the inner layer and coated with the outer layer. In accordance with an exemplary embodiment, the catheter wall portion, for example, has a thickness of 0.15 mm and a catheter diameter of 0.3 mm.

The shaft portion 201 of the catheter 200 of the present embodiment has a structure in which the hydrophilic member 33 ($\varphi 0.04$ mm) and the hydrophobic member 43 ($\varphi 0.04$ mm) are stacked. A resin-coated layer for preventing liquid circulation between the inner layer side and the outer layer side of the shaft portion 201 is unnecessary in this exemplary embodiment, and thus the wall portion of the catheter 200 of the present embodiment can be, for example, 0.08 mm and the catheter diameter can be, for example, 0.16 mm. Accordingly, the catheter 200 of the present embodiment can be, for example, 0.14 mm smaller in catheter diameter than the existing catheter.

As described above, the main body portion 20 constitutes the shaft portion 201 of the catheter 200.

In this configuration, the shaft portion 201 of the catheter 200 is capable of suppressing liquid circulation between the inner layer side and the outer layer side, for example, by means of nothing but the stacked structure of the hydrophilic member 33 and the hydrophobic member 43. In accordance with this exemplary embodiment, the catheter 200 does not require any resin-coated layer for preventing liquid circulation between the inner layer side and the outer layer side of the shaft portion 201, and thus the diameter of the catheter 200 can be reduced. As a result, the peripheral accessibility and torque transmission performance of the catheter can be improved. Also, in the case of a guiding catheter, a reduction in outer diameter is possible as compared with an existing catheter of the same inner diameter, and thus a puncture portion can be reduced in size. Further, an increase in inner diameter is possible as compared with an existing catheter of the same outer diameter, and thus a device with a larger outer diameter can be inserted through the lumen of the shaft portion 201.

Example of Application of Main Body Portion 20 to Sheath 300

Figure 6:
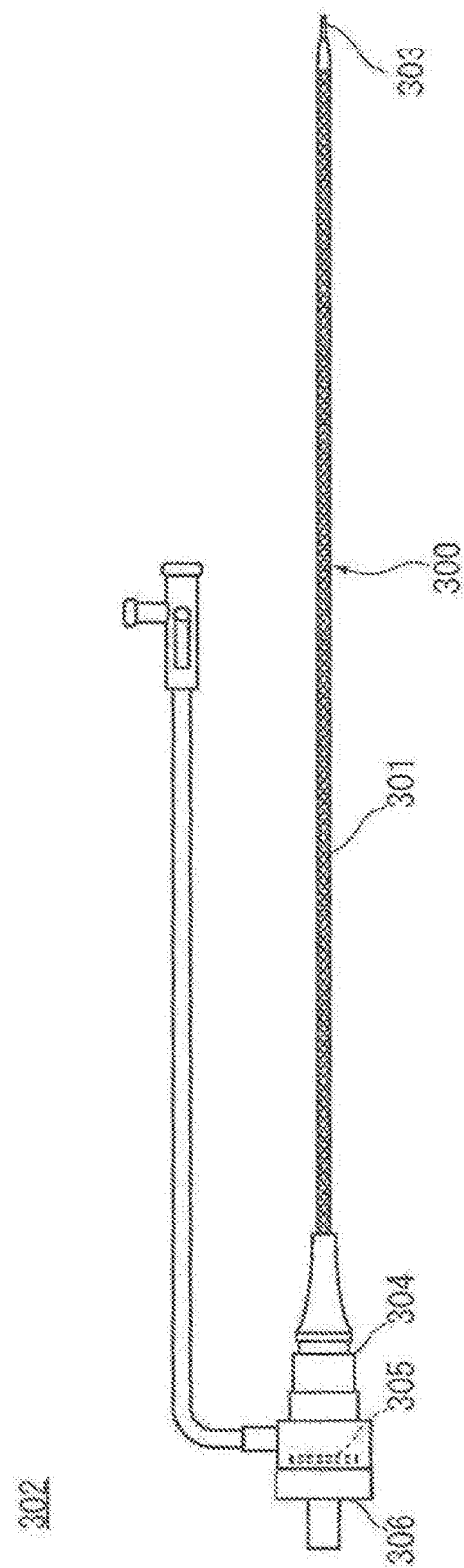
FIG. 6 is a diagram illustrating an example in which the main body portion is applied to a sheath tube of a sheath.

FIG. 6 is a diagram illustrating an example in which the main body portion 20 is applied to a sheath tube 301 of a sheath 300.

The illustrated sheath 300 is an introducer sheath 300.

A sheath percutaneously inserted into a body lumen is used so that an elongated body inserted into the body lumen is guided. It is preferable that the sheath has a small outer diameter, which is because a puncture site resulting from the sheath is less likely to lead to complications when the site is relatively small. Considering the relationship between the kink resistance of the sheath and the device dimension of insertion, the inner and outer diameters of the sheath are strictly limited.

Existing sheaths are resin-molded articles, and thus have the demerits (or limitations) of being limited in terms of thickness reduction and being prone to kinks.

In accordance with an exemplary embodiment, a sheath can be formed with a braided metal wire alone and without a resin-coated layer in order to achieve both kink resistance and thickness reduction. However, drug injection or the like can be performed through the sheath in some cases, and thus it is desired that no liquid circulates between the inner and outer layer sides of the sheath.

In accordance with an exemplary embodiment, the main body portion 20 described above is suitable for constituting the sheath tube 301 of the introducer sheath 300 to be percutaneously inserted into the body lumen 70.

As illustrated in FIG. 6, an introducer assembly 302 has the introducer sheath 300 securing an access route into a body-cavity and a dilator 303 assisting with insertion of the introducer sheath 300. The introducer sheath 300 is provided with the sheath tube 301, a sheath hub 304, and a hemostatic valve 305. The dilator 303 is inserted through the sheath tube 301 and the distal portion of the dilator 303 protrudes from the distal end of the sheath tube 301. The dilator 303 has a dilator hub 306 connected to the sheath hub 304.

In the sheath tube 301 of the introducer sheath 300, the first base portion 31 and the second base portion 41 have a plate shape as illustrated in FIGS. 2B to 2D. The hydrophilic member 33 and the hydrophobic member 43 are formed in a mesh shape.

The first base portion 31 and the second base portion 41 may have a wire shape as illustrated in FIG. 2A. The hydrophilic member 33 and the hydrophobic member 43 may be formed in a coil shape.

In accordance with an exemplary embodiment, the hydrophilic member 33 that has a mesh shape and the hydrophobic member 43 that has a coil shape may be stacked in the sheath tube 301 as illustrated in FIG. 2E. The hydrophilic member 33 that has a coil shape and the hydrophobic member 43 that has a mesh shape may be stacked in the sheath tube 301 as illustrated in FIG. 2F.

As illustrated in FIGS. 2A to 2F, the peripheral wall portion 21 is a structure that has at least two layers. The hydrophilic first layer 30 and the hydrophobic second layer 40 are sequentially stacked from the inner layer toward the outer layer. As for the hydrophilic first layer 30, the adjacent hydrophilic members 33 come into contact with each other as a result of swelling of the hydrophilic coating 32 caused by water, a body fluid, a drug solution, or the like. As a result, the peripheral wall portion 21 helps prevent liquid circulation between the inner layer side and the outer layer side. The hydrophobic second layer 40 blocks inflow of blood outside the introducer sheath 300 to the inner layer side.

In accordance with an exemplary embodiment, the peripheral wall portion 21 can be a three-layered structure in which the hydrophilic first layer 30, the hydrophobic second layer 40, and the hydrophilic first layer 30 are sequentially stacked from the inner layer toward the outer layer as illustrated in FIG. 3A. Considering an actual use of the introducer sheath 300, the hydrophilic first layer 30 is more preferable than the hydrophobic second layer 40 as the outermost layer, which enhances slidability with respect to the inner surface of the body lumen 70 in that the introducer sheath 300 is the medical instrument 10 that moves in the body lumen 70.

In accordance with an exemplary embodiment, the layered structure of the introducer sheath 300 may not be constant from the proximal portion to the distal portion. For example, the hydrophilic first layer 30, the hydrophobic second layer 40, and the hydrophilic first layer 30 may be sequentially stacked from the inner layer toward the outer layer on the distal side (stacked structure in FIG. 3A) with the hydrophobic second layer 40, the hydrophilic first layer 30, and the hydrophobic second layer 40 sequentially stacked from the inner layer toward the outer layer on the proximal side (stacked structure in FIG. 3C).

As described above, the main body portion 20 constitutes the sheath tube 301 of the introducer sheath 300 to be percutaneously inserted into the body lumen 70.

With this configuration, it is possible to provide the sheath tube 301 achieving both kink resistance and thickness reduction. The sheath tube 301 of the introducer sheath 300 is capable of suppressing liquid circulation between the inner layer side and the outer layer side, for example, by means of nothing but the stacked structure of the hydrophilic member 33 and the hydrophobic member 43. The introducer sheath 300 does not require any resin-coated layer for preventing liquid circulation between the inner layer side and the outer layer side of the sheath tube 301, and thus the relatively small-diameter and high-flexibility introducer sheath 300 can be obtained. As a result, the introducer sheath 300 can be used for thin blood vessels or puncture portion size reduction. Further, an increase in the inner diameter of the introducer sheath 300 is possible as compared with an existing introducer sheath of the same outer diameter, and thus a device with a larger outer diameter can be inserted through the lumen of the shaft portion 201.

Example of Application of Main Body Portion 20 to Stent 400

Figure 7A:
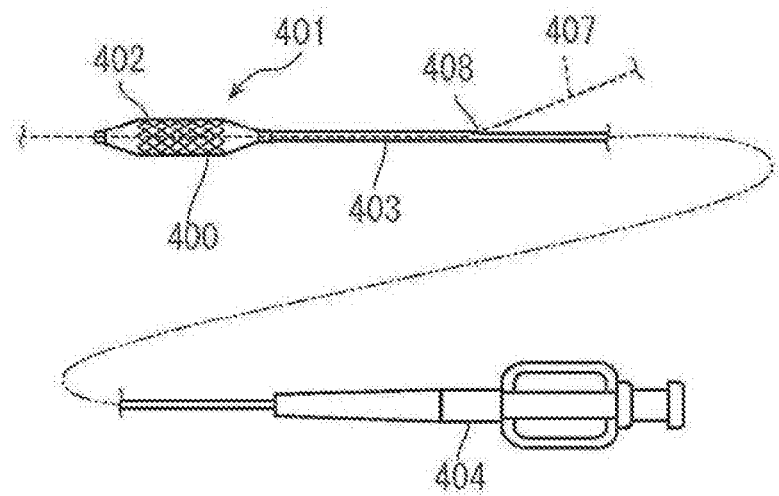
FIG. 7A is a diagram illustrating a balloon catheter placing a stent at a desired position in a body lumen with the main body portion applied to the stent.
Figure 7B:
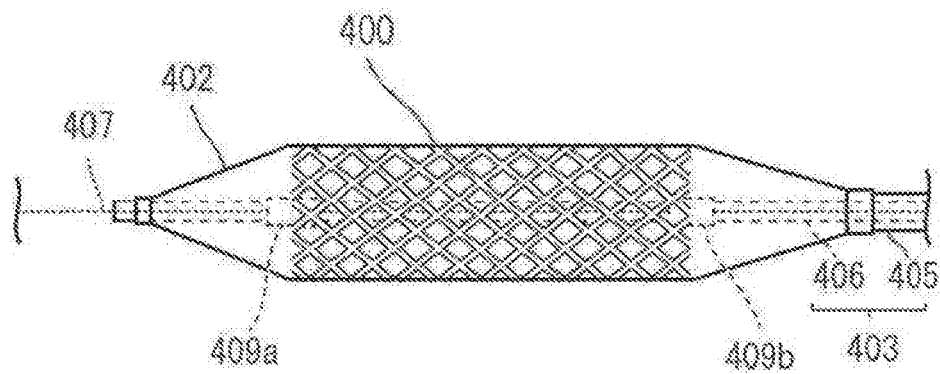
FIG. 7B is an enlarged view of the distal portion of the balloon catheter.
Figure 7C:
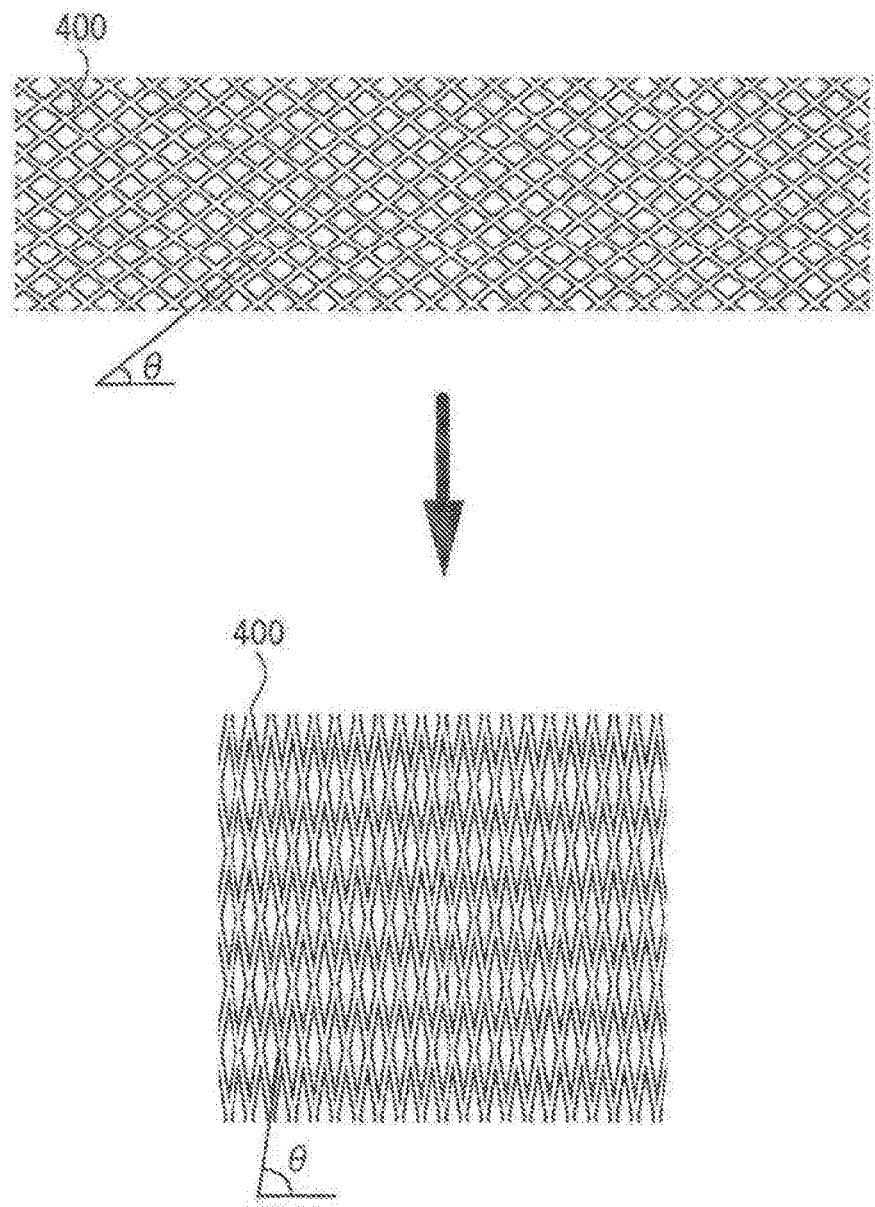
FIG. 7C is a plan view illustrating the pre-expanded and post-expanded shapes of the stent.

FIG. 7A is a diagram illustrating a balloon catheter 401 placing a stent 400 at a desired position in the body lumen 70 with the main body portion 20 applied to the stent 400. FIG. 7B is an enlarged view of the distal portion of the balloon catheter 401. FIG. 7C is a plan view illustrating the pre-expanded and post-expanded shapes of the stent 400.

The gap parts illustrated in FIGS. 7A to 7C are exaggerated in size so that grasping of the mesh shape of the stent 400 is facilitated. As described above, the first base portions 31 are disposed at the pitch p1 and the second base portions 41 are disposed at the pitch p2.

Stent placement for placing a stent is performed as a method for treating a lesion area (stenosed site) formed in a blood vessel or the like. In general, a balloon catheter is used as a delivery device during stent placement into a lesion area.

In a non-expanded state, the stent is held (mounted) on the outer surface of a balloon folded on the outer periphery of a shaft. Once the stent is delivered to the lesion area, the stent is expanded by the balloon and placed into the lesion area in an expanded state. As a result of the stent placement into the lesion area, the lesion area is widened by the expansion force of the stent. Examples of the stent include a balloon expandable stent for use in coronary arteries and a balloon expandable stent for use in peripheral blood vessels.

In the case of an existing stent, liquid circulation occurs between the inner and outer layers of the stent after the stent is placed into a body lumen. Accordingly, the drug that is applied to the outermost layer of the stent flows out to the inner layer side of the stent without transition to a target lesion area. In addition, the drug that is applied to the innermost layer of the stent flows out to the outer layer side of the stent without transition to the target lesion area. As a result, problems can arise from a decline in the effects of the drugs on the outermost and innermost layers.

The main body portion 20 described above is suitable for constituting the stent 400 placed into the body lumen 70.

In the balloon catheter 401 for stent delivery, the stent 400 is mounted on a balloon 402 that is in a deflated state as illustrated in FIG. 7A. The balloon catheter 401 has an elongated shaft 403, the inflatable and deflatable balloon 402 provided on the distal side of the shaft 403, and a hub 404 fixed to the proximal end of the shaft 403.

As illustrated in FIG. 7B, the shaft 403 has an outer tube 405 and an inner tube 406 inserted through the lumen of the outer tube 405. A hollow tube shaped body constitutes the outer tube 405. An inflation lumen through which an inflation fluid for inflating the balloon 402 circulates is formed between the outer tube 405 and the inner tube 406. A guide wire lumen is formed in the inner tube 406. A guide wire 407, which guides the balloon 402 to a lesion area, is inserted through the guide wire lumen.

As illustrated in FIG. 7A, the balloon catheter 401 is configured as a so-called rapid exchange-type catheter in which the guide wire 407 is introduced into the inner tube 406 via an opening portion 408 for a guide wire, which is formed between the distal side and the proximal side of the shaft 403. Alternatively, the balloon catheter 401 may be configured as a so-called over-the-wire catheter.

The distal portion of the inner tube 406 penetrates the inner portion of the balloon 402 and is open on the distal side that is beyond the balloon 402 as illustrated in FIG. 7B. In accordance with an exemplary embodiment, the inner tube 406 can be provided with contrast markers 409a and 409b.

The proximal portion of the balloon 402 is fixed to the distal portion of the outer tube 405 and the distal portion of the balloon 402 is fixed to the distal portion of the inner tube 406. In the deflated state, the balloon 402 is folded so as to be wound around the outer periphery of the inner tube 406.

In accordance with an exemplary embodiment, the first base portion 31 and the second base portion 41 of the stent 400 have a plate shape as illustrated in FIGS. 2B to 2D. The hydrophilic member 33 and the hydrophobic member 43 are formed in a mesh shape and constitute a stent strut.

As illustrated in FIG. 3B, the peripheral wall portion 21 has a three-layered structure. The hydrophilic first layer 30, the hydrophobic second layer 40, and the hydrophobic second layer 40 are sequentially stacked from the inner layer toward the outer layer. The hydrophobic second layer 40, the hydrophilic first layer 30, and the hydrophobic second layer 40 may be sequentially stacked from the inner layer toward the outer layer, as illustrated in FIG. 3C, in the peripheral wall portion 21. As for the hydrophilic first layer 30, the adjacent hydrophilic members 33 come into contact with each other as a result of swelling of the hydrophilic coating 32 caused by blood. As a result, the peripheral wall portion 21 helps prevent liquid circulation between the inner layer side and the outer layer side. Considering an actual use of the stent 400, the hydrophobic second layer 40 is more preferable than the hydrophilic first layer 30 as the outermost layer to reduce the possibility of deviation with respect to the inner surface of the body lumen 70 in that the stent 400 needs to be pressure-joined to a blood vessel wall.

In accordance with an exemplary embodiment, the innermost layer of the stent 400 is coated with a drug (antiplatelet drug) preventing thrombus formation and biodegradable plastic. The drug can be released slowly by gradual degradation of the biodegradable plastic.

In general, antiplatelet drug is taken, for example, for three month to 12 months or more, for stent thrombosis prevention in a case where the stent 400 is placed in a blood vessel. Since the stent 400 has sustained drug-release properties, the stent 400 eliminates the need for patients' medication and is capable of making a contribution by preventing a patient from forgetting to take his or her medicine and improving the patient's quality of life (QOL).

In accordance with an exemplary embodiment, the first base portion 31 and the second base portion 41 constituting the stent 400 may have a wire shape as illustrated in FIG. 2A. The hydrophilic member 33 and the hydrophobic member 43 may be formed in a coil shape.

As illustrated in FIG. 7C, the stent 400 changes from the pre-expanded shape illustrated on the upper side to the post-expanded shape illustrated on the lower side. Once the balloon 402 is inflated and the stent 400 is increased in diameter as a result, the longitudinal length of the stent 400 (length in the left-right direction in the drawing) decreases.

It is possible to reduce the gap of the stent strut by increasing the mesh angle that is indicated by reference sign θ in the drawing. In a case where the hydrophilic member 33 and the hydrophobic member 43 are formed in a coil shape, the gap of the stent strut can be reduced by an increase in coil angle.

The stent 400 is placed at a target site in the body lumen 70 by the balloon catheter 401. The gap of the stent strut decreases after the stent 400 is expanded. Further, the adjacent hydrophilic members 33 come into contact with each other as a result of swelling of the hydrophilic coating 32 caused by blood. As a result, the stent 400 blocks blood flow from the inner layer side to the outer layer side. Meanwhile, blood flow can be ensured in the stent 400.

As described above, the main body portion 20 constitutes the stent 400 placed into the body lumen 70.

In this configuration, the stent 400 placed into the body lumen 70 is capable of suppressing liquid circulation between the inner layer side and the outer layer side, for example, by means of nothing but the stacked structure of the hydrophilic member 33 and the hydrophobic member 43. As for the expandable stent 400 ensuring blood flow, a drug preventing neointima growth can be applied to the outermost layer of the stent 400 and a drug preventing thrombus formation can be applied to the innermost layer of the stent 400. As a result of the liquid circulation prevention between the inner and outer layers of the stent 400, transition to a target lesion area can be achieved for each of the drugs on the outermost and innermost layers. Accordingly, the drugs are efficacious in a suitable manner based on the absence of liquid circulation and performance improvement is achieved in terms of neointima growth prevention and thrombus formation prevention.

Example of Application of Main Body Portion 20 to Flow Diverter Stent 450

Figure 8A:
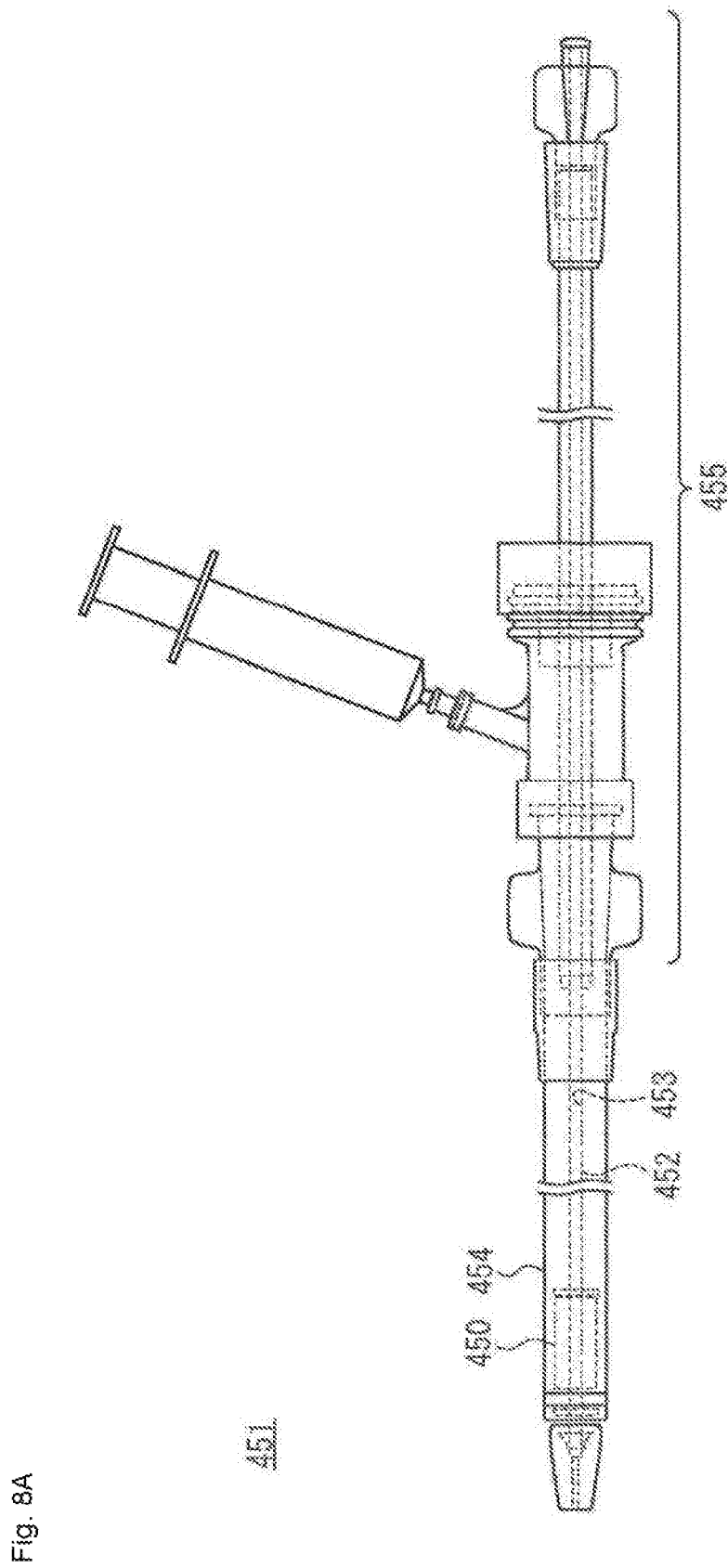
FIG. 8A is a diagram illustrating a self-expandable stent delivery system for placing a flow diverter stent at a desired position in the body lumen, in which the main body portion is used to form the flow diverter stent.
Figure 8B:
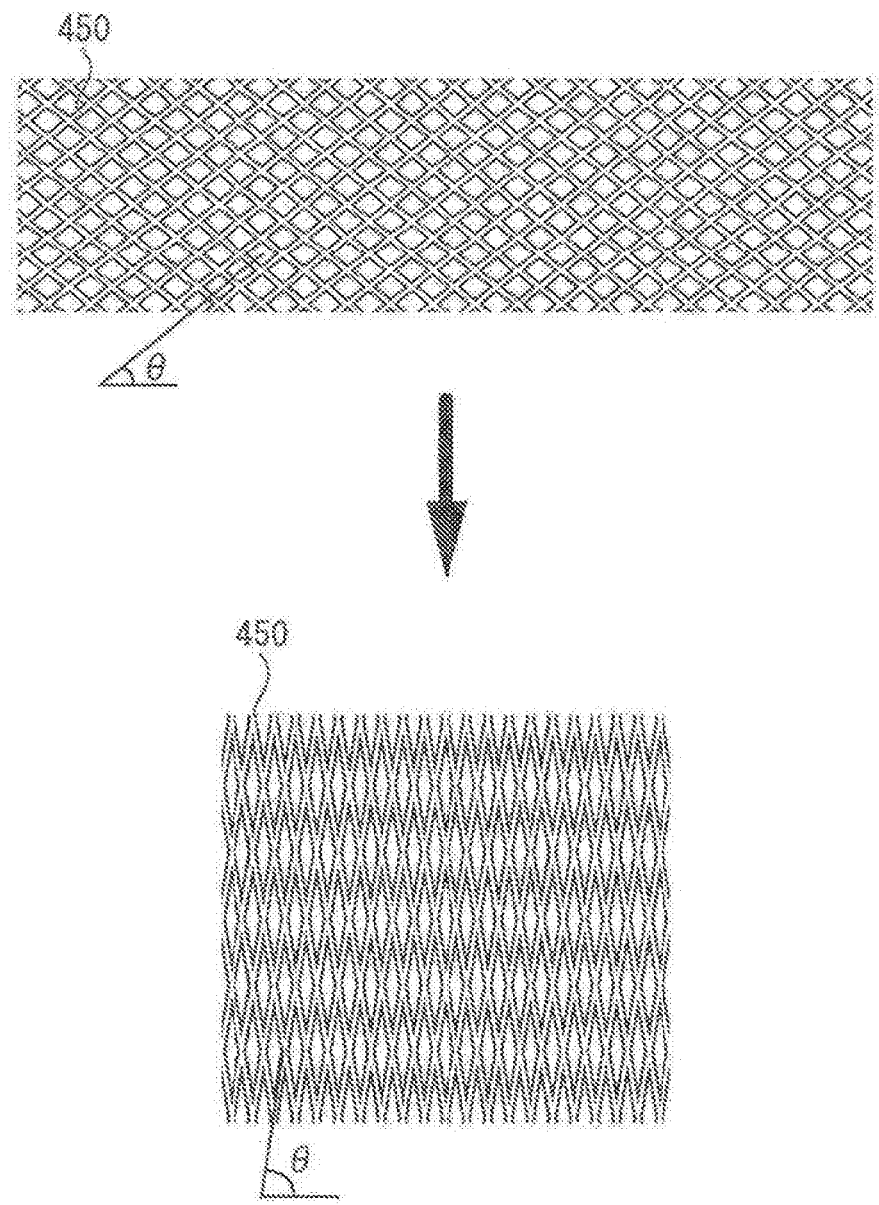
FIG. 8B is a plan view illustrating the pre-self-expanded and post-self-expanded shapes of the flow diverter stent.
Figure 8C:
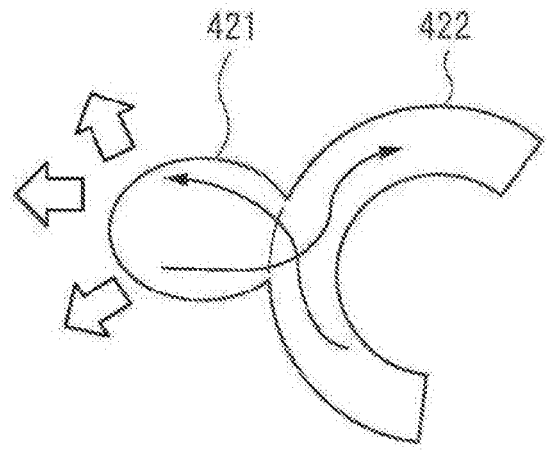
FIG. 8C is a diagram schematically illustrating a state of blood flow between an aneurysm and a parent blood vessel.
Figure 8D:
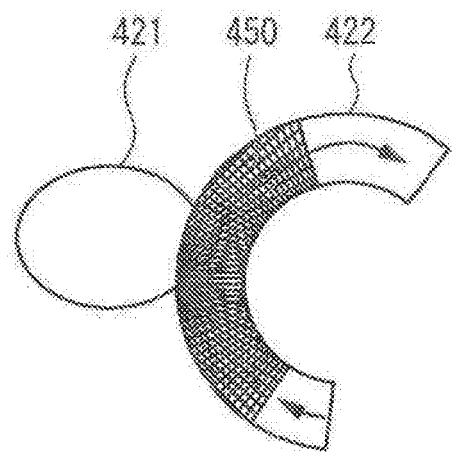
FIG. 8D is a diagram schematically illustrating a state where the flow diverter stent is placed for blocking of the blood flow between the aneurysm and the parent blood vessel.

FIG. 8A is a diagram illustrating a self-expandable stent delivery system 451 for placing a flow diverter stent 450 at a desired position in the body lumen 70 in which the main body portion 20 is used to form the flow diverter stent 450. FIG. 8B is a plan view illustrating the pre-self-expanded and post-self-expanded shapes of the flow diverter stent 450. FIG. 8C is a diagram schematically illustrating a state of blood flow between an aneurysm 421 and a parent blood vessel 422. FIG. 8D is a diagram schematically illustrating a state where the flow diverter stent 450 is placed for blocking of the blood flow between the aneurysm 421 and the parent blood vessel 422.

The gap parts illustrated in FIG. 8B are exaggerated in size so that grasping of the mesh shape of the flow diverter stent 450 is facilitated. As described above, the first base portions 31 are disposed at the pitch p1 and the second base portions 41 are disposed at the pitch p2.

In recent years, flow diverter placement as well as coil-based embolization has attracted attention as a cerebrovascular aneurysm treatment method. The flow diverter placement is a treatment method for causing aneurysm clotting and preventing rupture by means of flow diverter stent placement between an aneurysm and a parent blood vessel and blocking of blood flow from the parent blood vessel into the aneurysm.

An existing flow diverter stent has a precise blade mesh structure in which blood flow between an aneurysm and a parent blood vessel is blocked by surface tension. However, blood circulation occurs to some extent between the aneurysm and the parent blood vessel, and thus a relatively long time is required for the aneurysm clotting. The aneurysm may rupture before clotting, and thus it is necessary to block the blood flow between the aneurysm and the parent blood vessel.

In accordance with an exemplary embodiment, the main body portion 20 described above is suitable for constituting the flow diverter stent 450 for blocking blood flow between the inner and outer layer sides and for use in blocking of blood flow between the aneurysm 421 and the parent blood vessel 422.

In accordance with an exemplary embodiment, the flow diverter stent 450 is a self-expandable stent. As illustrated in FIG. 8A, the self-expandable stent delivery system 451 has an inner tube 452, an outer tube 454, the flow diverter stent 450, and a hand operation unit 455. The inner tube 452 is provided with a guide wire lumen 453 through which a guide wire is inserted. The outer tube 454 is disposed so as to cover the distal portion side of the inner tube 452. The flow diverter stent 450 is disposed between the distal portion of the inner tube 452 and the distal portion of the outer tube 454. The flow diverter stent 450 is released from the space between the inner tube 452 and the outer tube 454, expanded, and deformed as the outer tube 454 moves. The hand operation unit 455 is disposed on the proximal side of the inner tube 452 and configured to be grippable, for example, by a user. The self-expandable stent delivery system 451 is capable of inserting the inner tube 452 and the outer tube 454 along the guide wire into an intra-body target site. After the flow diverter stent 450 is released and placed into the body, the outer tube 454 and the inner tube 452 are removed to the outside the body.

The first base portion 31 and the second base portion 41 of the flow diverter stent 450 have a plate shape as illustrated in FIGS. 2B to 2D. The hydrophilic member 33 and the hydrophobic member 43 are formed in a mesh shape and constitute a stent strut.

As illustrated in FIG. 3B, the peripheral wall portion 21 has a three-layered structure. The hydrophilic first layer 30, the hydrophobic second layer 40, and the hydrophobic second layer 40 are sequentially stacked from the inner layer toward the outer layer. The hydrophobic second layer 40, the hydrophilic first layer 30, and the hydrophobic second layer 40 may be sequentially stacked from the inner layer toward the outer layer, as illustrated in FIG. 3C, in the peripheral wall portion 21. As for the hydrophilic first layer 30, the adjacent hydrophilic members 33 come into contact with each other as a result of swelling of the hydrophilic coating 32 caused by blood. As a result, the peripheral wall portion 21 helps prevent liquid circulation between the inner layer side and the outer layer side. Considering an actual use of the flow diverter stent 450, the hydrophobic second layer 40, for example, is more preferable than the hydrophilic first layer 30 as the outermost layer to reduce the possibility of deviation with respect to the inner surface of the body lumen 70 in that the flow diverter stent 450 needs to be pressure-joined to a blood vessel wall.

The innermost layer of the flow diverter stent 450 is coated with a drug (antiplatelet drug) preventing thrombus formation and biodegradable plastic. The drug can be released slowly by gradual degradation of the biodegradable plastic.

In general, an antiplatelet drug is taken, for example, for three months to 12 months or more, for stent thrombosis prevention in a case where the flow diverter stent 450 is placed in a blood vessel. Since the flow diverter stent 450 has sustained drug-release properties, the flow diverter stent 450 eliminates the need for patients' medication and is capable of making a contribution by preventing a patient from forgetting to take his or her medicine and improving the patient's quality of life (QOL).

The first base portion 31 and the second base portion 41 of the flow diverter stent 450 may have a wire shape as illustrated in FIG. 2A. The hydrophilic member 33 and the hydrophobic member 43 may be formed in a coil shape.

As illustrated in FIG. 8B, the flow diverter stent 450 changes from the pre-self-expanded shape illustrated on the upper side to the post-self-expanded shape illustrated on the lower side. Once a self-increase in the diameter of the flow diverter stent 450 occurs, the longitudinal length of the flow diverter stent 450 (length in the left-right direction in the drawing) decreases. It is possible to reduce the gap of the stent strut by increasing the mesh angle that is indicated by reference sign θ in the drawing. In a case where the hydrophilic member 33 and the hydrophobic member 43 are formed in a coil shape, the gap of the stent strut can be reduced by an increase in coil angle. The flow diverter stent 450 helps prevent liquid circulation between the inner layer side and the outer layer side even after self-expansion.

Blood flow occurs between the aneurysm 421 and the parent blood vessel 422 as indicated by the solid-line arrows in FIG. 8C, and then the aneurysm 421 becomes relatively large as indicated by the white arrows in FIG. 8C.

As illustrated in FIG. 8D, the flow diverter stent 450 is placed between the aneurysm 421 and the parent blood vessel 422. The gap of the stent strut decreases after self-expansion of the flow diverter stent 450. Further, the adjacent hydrophilic members 33 come into contact with each other as a result of swelling of the hydrophilic coating 32 caused by blood. As a result, the flow diverter stent 450 blocks blood flow from the inner layer side to the outer layer side, that is, from the parent blood vessel 422 side to the aneurysm 421 side. Meanwhile, blood flow is ensured in the flow diverter stent 450. By blocking the aneurysm 421 from the parent blood vessel 422, it is possible to cause the aneurysm 421 to clot relatively early and help prevent rupture.

As described above, the main body portion 20 constitutes the flow diverter stent 450 blocking blood flow between the inner and outer layer sides and used for blocking of blood flow between the aneurysm 421 and the parent blood vessel 422.

In this configuration, the flow diverter stent 450 is capable of suppressing liquid circulation between the inner layer side and the outer layer side by means of nothing but the stacked structure of the hydrophilic member 33 and the hydrophobic member 43. The flow diverter stent 450 is capable of blocking blood flow from the parent blood vessel 422 to the aneurysm 421 side and maintaining blood flow in the flow diverter stent 450. The flow diverter stent 450 is capable of causing the aneurysm 421 to clot relatively early and preventing rupture by blocking the aneurysm 421 from the parent blood vessel 422.

A drug preventing neointima growth can be applied to the outermost layer of the flow diverter stent 450 and a drug preventing thrombus formation can be applied to the innermost layer of the flow diverter stent 450 as in the case of the stent 400. As a result of the liquid circulation prevention between the inner and outer layers of the flow diverter stent 450, transition to a target lesion area can be achieved for each of the drugs on the outermost and innermost layers. Accordingly, the drugs are efficacious in a suitable manner based on the absence of liquid circulation and performance improvement is achieved in terms of neointima growth prevention and thrombus formation prevention.

Stent graft placement is known as an aortic aneurysm treatment method. The stent graft placement is means for preventing aneurysm rupture, for example, by means of stent-based support and placement of a graft that reinforces a blood vessel wall from the inside. In accordance with an exemplary embodiment, the graft can be an artificial blood vessel in which water-repellent fibers are braided.

The flow diverter stent 450 of the present embodiment can be used as a stent graft since the flow diverter stent 450 helps prevent liquid circulation between the inner layer and the outer layer. In this case, no graft as a fiber layer is necessary, and thus a small-diameter and high-flexibility stent graft can be obtained. As a result, the stent graft can be used for thin blood vessels as well.

Example of Application of Main Body Portion 20 to Embolic Material 500

Figure 9:
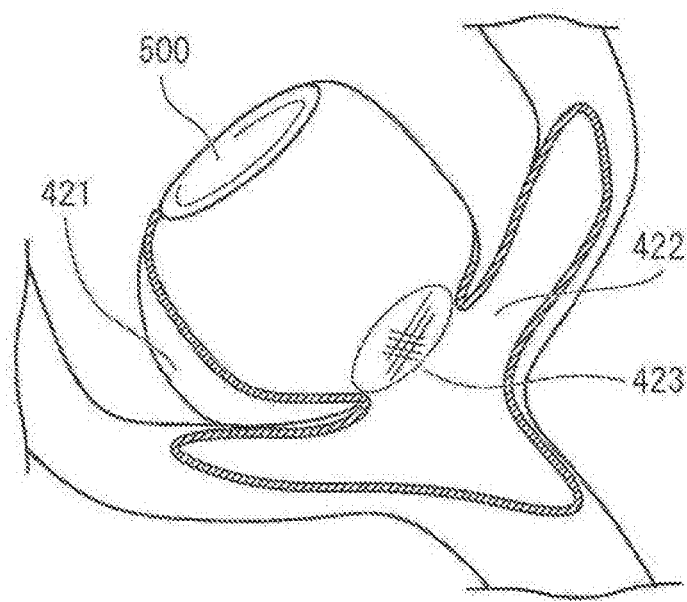
FIG. 9 is a diagram schematically illustrating a state where an embolic material to which the main body portion is applied is placed in the aneurysm so that an inlet port from the parent blood vessel to the aneurysm is blocked.

FIG. 9 is a diagram schematically illustrating a state where an embolic material 500 to which the main body portion 20 is applied is placed in the aneurysm 421 so that an inlet port 423 from the parent blood vessel 422 to the aneurysm 421 is blocked.

As described above, coil-based embolization is known as a cerebrovascular aneurysm treatment method. Even with an aneurysm filled with coils, however, an inlet port from a parent blood vessel to the aneurysm cannot be blocked with ease due to the presence of the minute gaps between the coils. Blood circulation occurs to some extent between the aneurysm and the parent blood vessel, and thus a relatively long time can be required for aneurysm clotting. The aneurysm may rupture before clotting, and thus it is necessary to block the blood flow between the aneurysm and the parent blood vessel. The main body portion 20 described above is suitable for constituting the embolic material 500 blocking blood flow between the inner and outer layer sides and used for blocking the inlet port 423 from the parent blood vessel 422 to the aneurysm 421 by being placed into the aneurysm 421.

As illustrated in FIG. 9, the embolic material 500 is formed in a mesh shape. The peripheral wall portion 21 has a three-layered structure as in the case of the stent 400 described above. The hydrophilic first layer 30, the hydrophobic second layer 40, and the hydrophobic second layer 40 are sequentially stacked from the inner layer toward the outer layer (stacked structure in FIG. 3B). The hydrophobic second layer 40, the hydrophilic first layer 30, and the hydrophobic second layer 40 may be sequentially stacked from the inner layer toward the outer layer in the peripheral wall portion 21 (stacked structure in FIG. 3C). As for the hydrophilic first layer 30, the adjacent hydrophilic members 33 come into contact with each other as a result of swelling of the hydrophilic coating 32 caused by blood. As a result, the peripheral wall portion 21 helps prevent blood circulation at the inlet port 423. Considering an actual use of the embolic material 500, the hydrophobic second layer 40 is more preferable than the hydrophilic first layer 30 as the outermost layer to reduce the possibility of deviation with respect to the inner surface of the body lumen 70 in that the embolic material 500 needs to be pressure-joined to a blood vessel wall.

In accordance with an exemplary embodiment, the innermost layer of the embolic material 500 is coated with a drug promoting blood coagulation and biodegradable plastic. The drug can be released, for example, slowly by gradual degradation of the biodegradable plastic.

Since the embolic material 500 has sustained drug-release properties, the embolic material 500 helps eliminate the need for patients' medication and is capable of making a contribution by preventing a patient from forgetting to take his or her medicine and improving the patient's quality of life (QOL).

As illustrated in FIG. 9, the inlet port 423 from the parent blood vessel 422 to the aneurysm 421 is blocked by the mesh-shaped embolic material 500 being placed into the aneurysm 421. The adjacent hydrophilic members 33 come into contact with each other as a result of swelling of the hydrophilic coating 32 caused by blood. As a result, the embolic material 500 blocks blood flow from the inlet port 423 to the aneurysm 421 side. By blocking the aneurysm 421 from the parent blood vessel 422, it is possible to cause the aneurysm 421 to clot relatively early and prevent rupture.

As described above, the main body portion 20 is suitable for constituting the embolic material 500 blocking blood flow between the inner and outer layer sides and used for blocking the inlet port 423 from the parent blood vessel 422 to the aneurysm 421 by being placed into the aneurysm 421.

In this configuration, the embolic material 500 is capable of suppressing liquid circulation between the inner layer side and the outer layer side, for example, by means of nothing but the stacked structure of the hydrophilic member 33 and the hydrophobic member 43 and blocks blood flow from the inlet port 423 to the aneurysm 421 side. The embolic material 500 is capable of causing the aneurysm 421 to clot relatively early and preventing rupture by blocking the aneurysm 421 from the parent blood vessel 422.

In accordance with an exemplary embodiment, a drug promoting blood coagulation can be applied to the innermost layer of the embolic material 500. As a result of the liquid circulation prevention between the inner and outer layers of the embolic material 500, transition to a target lesion area is achieved for the drug on the innermost layer. Accordingly, the drug is efficacious in a suitable manner based on the absence of liquid circulation and performance improvement is achieved in terms of blood coagulation promotion.

Example of Application of Main Body Portion 20 to Cover Member 600 for Drug-Coated Balloon 601

Figure 10A:
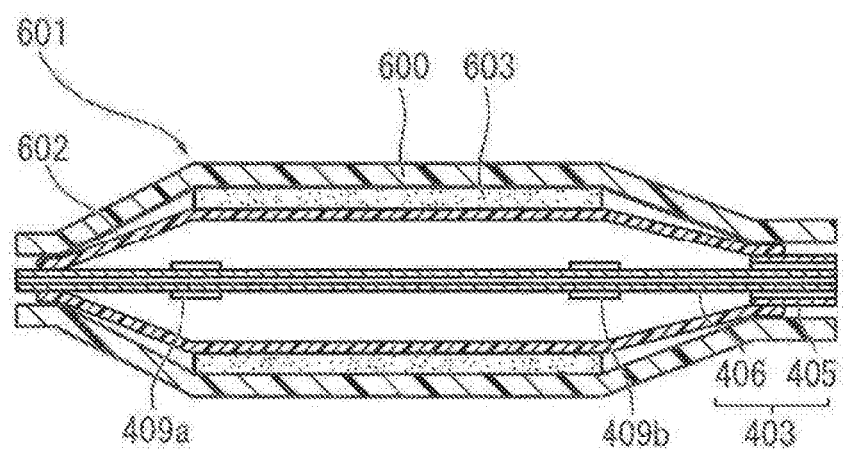
FIG. 10A is an enlarged cross-sectional view illustrating the distal portion of a drug-coated balloon to which a cover member to which the main body portion is applied is attached.
Figure 10B:
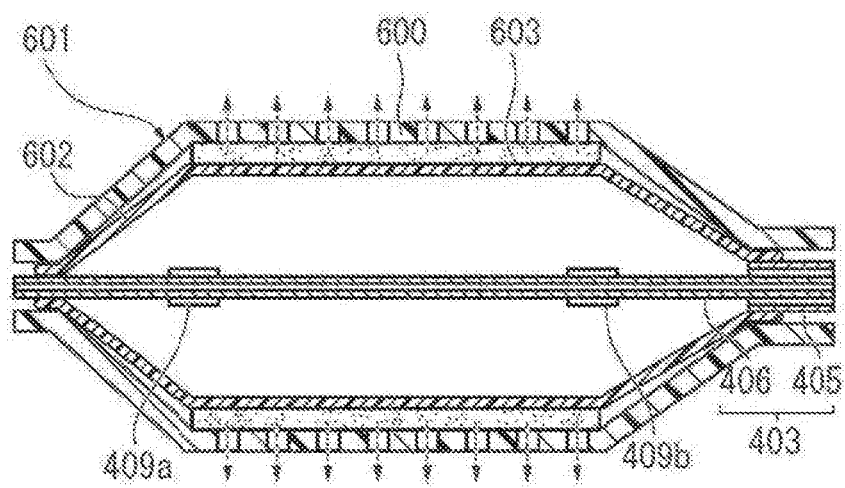
FIG. 10B is a cross-sectional view illustrating a state where the cover member is increased in diameter by a balloon being inflated.
Figure 10C:
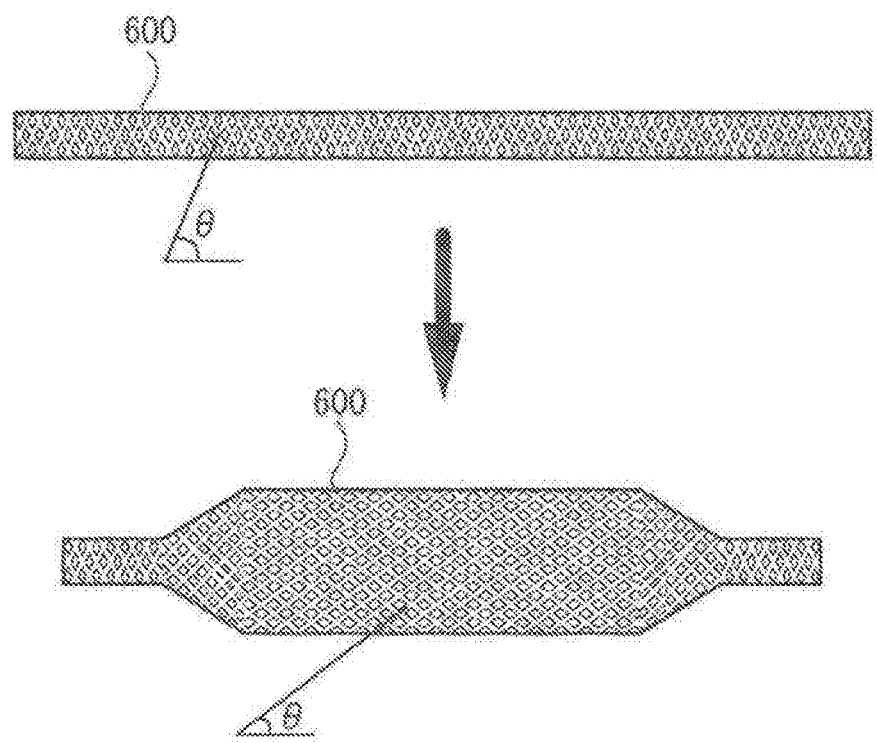
FIG. 10C is a plan view illustrating the pre-expanded and post-expanded shapes of the cover member.

FIG. 10A is an enlarged cross-sectional view illustrating the distal portion of a drug-coated balloon 601 to which a cover member 600 to which the main body portion 20 is applied is attached. FIG. 10B is a cross-sectional view illustrating a state where the cover member 600 is increased in diameter by a balloon 602 being inflated. FIG. 10C is a plan view illustrating the pre-expanded and post-expanded shapes of the cover member 600. Regarding the configuration of the balloon 602, members that are in common with those illustrated in FIG. 7B are denoted by the same reference signs with descriptions of the members partially omitted.

A drug-coated balloon (DCB) is a drug delivery system (DDS) applying a drug to a target blood vessel site with the drug applied to the surface of a balloon. The drug applied to the balloon flows out when the drug-coated balloon is taken out from a holder tube or accesses the target site. Accordingly, at present, effective drug application or release is impossible at target sites.

In accordance with an exemplary embodiment, the main body portion 20 described above is suitable for constituting the tubular cover member 600 used so that the periphery of the balloon 602 is covered in the drug-coated balloon 601 in which a drug 603 is applied to the surface of the balloon 602. The cover member 600 operates the balloon 602 with the balloon 602 positioned at a target site. As a result, the cover member 600 allows the drug 603 positioned on the inner layer side of the cover member 600 to be released to the outer layer side of the cover member 600.

As illustrated in FIGS. 10A to 10C, the first base portion 31 and the second base portion 41 of the cover member 600 have a plate shape. The hydrophilic member 33 and the hydrophobic member 43 are formed in a mesh shape.

As illustrated in FIG. 3A, the peripheral wall portion 21 has a three-layered structure. The hydrophilic first layer 30, the hydrophobic second layer 40, and the hydrophilic first layer 30 are sequentially stacked from the inner layer toward the outer layer. The hydrophobic second layer 40, the hydrophilic first layer 30, and the hydrophilic first layer 30 may be sequentially stacked from the inner layer toward the outer layer, as illustrated in FIG. 3D, in the peripheral wall portion 21. As for the hydrophilic first layer 30, the adjacent hydrophilic members 33 come into contact with each other as a result of swelling of the hydrophilic coating 32 caused by a drug solution or water. As a result, the peripheral wall portion 21 helps prevent liquid circulation between the inner layer side and the outer layer side. Considering an actual use of the cover member 600, the hydrophilic first layer 30 is more preferable than the hydrophobic second layer 40 as the outermost layer to enhance slidability with respect to the inner surface of the body lumen 70 in that the cover member 600 is the medical instrument 10 that moves in the body lumen 70.

The first base portion 31 and the second base portion 41 of the cover member 600 may have a wire shape as illustrated in FIG. 2A. The hydrophilic member 33 and the hydrophobic member 43 may be formed in a coil shape.

As illustrated in FIG. 10C, the cover member 600 changes from the pre-expanded shape illustrated on the upper side to the post-expanded shape illustrated on the lower side. When the balloon 602 is inflated and the cover member 600 is increased in diameter as a result, the longitudinal length of the cover member 600 (length in the left-right direction in the drawing) decreases or both end parts become denser. The gap can be increased in diameter and enlarged by the mesh angle that is indicated by reference sign θ in the drawing being reduced. In a case where the hydrophilic member 33 and the hydrophobic member 43 are formed in a coil shape, the gap can be enlarged by a reduction in coil angle.

The layer of the drug 603 is disposed between the outer peripheral surface of the balloon 602 and the inner peripheral surface of the cover member 600.

As illustrated in FIG. 10A, the cover member 600 covers the periphery of the balloon 602 of the drug-coated balloon 601 in a state where the balloon 602 is closed. Since the layer of the drug 603 is covered by the cover member 600, the drug 603 is prevented from flowing out when the drug-coated balloon 601 is taken out from a holder tube or accesses a target site in a blood vessel.

As illustrated in FIG. 10B, the balloon 602 is operated once the balloon 602 reaches the target site. Once the balloon 602 is inflated and the cover member 600 is increased in diameter as a result, the mesh angle θ decreases and the gap becomes relatively large. The space between the adjacent hydrophilic members 33 and the space between the adjacent hydrophobic members 43 are expanded. As a result, the drug 603 is released from the inner layer side of the cover member 600 toward the outer layer side of the cover member 600 and transition to the target site occurs. As a result, the drug 603 can be effectively applied or released at the target site.

As described above, the main body portion 20 constitutes the tubular cover member 600 used so that the periphery of the balloon 602 is covered in the drug-coated balloon 601 in which the drug 603 is applied to the surface of the balloon 602. The cover member 600 operates the balloon 602 with the balloon 602 positioned at a target site. As a result, the cover member 600 allows the drug 603 positioned on the inner layer side to be released to the outer layer side.

With this configuration, the drug 603 applied to the balloon 602 does not flow out when the drug-coated balloon 601 is taken out from a holder tube or accesses a target site in a blood vessel. Accordingly, the drug 603 can be effectively applied or released at the target site.

Although examples of application of the main body portion 20 have been described above, the disclosure is not limited to this case. The disclosure can be widely applied to the medical instrument 10 for controlling liquid circulation through the peripheral wall portion 21 by radially laminating the first layer 30 on which the hydrophilic member 33 is disposed and the second layer 40 on which the hydrophobic member 43 is disposed.

The detailed description above describes embodiments of a medical instrument having a hydrophilic member and a hydrophobic member stacked. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical instrument comprising:
a main body portion having a center hole and a radially outward space partitioned by a tubular peripheral wall portion;
the tubular peripheral wall portion including at least:
a first layer having a hydrophilic member including a first base portion and a hydrophilic coating formed on the first base portion;
a second layer having a hydrophobic member including a second base portion and a hydrophobic coating formed on the second base portion; and
the first layer and the second layer being stacked along a radial direction; and
wherein when the hydrophilic coating is swollen, adjacent hydrophilic members come into contact with each other so that a first liquid in the center hole and a second liquid present in the radially outward space are prevented from circulating through the tubular peripheral wall portion.

2. The medical instrument according to claim 1, wherein the first base portion is disposed at a pitch configured to allow the swollen hydrophilic coatings of the adjacent hydrophilic members to be in contact with each other.

3. The medical instrument according to claim 1, wherein the second base portion is disposed at a pitch configured to set a space between the hydrophobic coatings of the adjacent hydrophobic members to a dimension smaller than a gap through which the first liquid and the second liquid pass.

4. The medical instrument according to claim 1, wherein the first base portion and the second base portion have a wire shape or a plate shape.

5. The medical instrument according to claim 1, wherein the hydrophilic member and the hydrophobic member have a coil shape, a ring shape, or a mesh shape.

6. The medical instrument according to claim 1, wherein the main body portion constitutes a shaft portion of a catheter.

7. The medical instrument according to claim 1, wherein the main body portion constitutes a sheath tube of a sheath configured to be percutaneously inserted into a body lumen.

8. The medical instrument according to claim 1, wherein the main body portion constitutes a stent configured to be placed into a body lumen.

9. The medical instrument according to claim 1, wherein the main body portion constitutes a flow diverter stent configured to block blood flow between an inner layer side and an outer layer side and is configured for use in blocking of blood flow between an aneurysm and a parent blood vessel.

10. The medical instrument according to claim 1, wherein the main body portion constitutes an embolic material configured to block blood flow between an inner layer side and an outer layer side and is configured to be placed into an aneurysm and used for blocking an inlet port from a parent blood vessel to the aneurysm.

11. The medical instrument according to claim 1, wherein the main body portion constitutes a tubular cover member configured to be used in such a manner as to cover a periphery of a drug-coated balloon including a balloon and a drug applied to a surface of the balloon, and the cover member is configured to allow the drug on an inner layer side of the cover member to be released to an outer layer side of the cover member when the balloon is operated in a state where the balloon is positioned at a target site.

12. The medical instrument according to claim 1, further comprising:

two or more of the first layer and one or more of the second layer; or two or more of the second layer and one or more of the first layer.

13. A medical instrument comprising:

an elongated tubular peripheral wall portion having a central lumen, the tubular peripheral wall portion including at least:

a first braided layer having a hydrophilic member including a first base portion and a hydrophilic coating formed on the first base portion; and a second braided layer having a hydrophobic member including a second base portion and a hydrophobic coating formed on the second base portion, and wherein the first braided layer and the second braided layer are stacked along a radial direction; and wherein when the hydrophilic coating is swollen, adjacent hydrophilic members come into contact with each other so that a first liquid in the central lumen and a second liquid present in a radially outward space are prevented from circulating through the tubular peripheral wall portion.

14. The medical instrument according to claim 13, wherein the first base portion is disposed at a pitch configured to allow the swollen hydrophilic coatings of the adjacent hydrophilic members to be in contact with each other; and wherein the second base portion is disposed at a pitch configured to set a space between the hydrophobic coatings of the adjacent hydrophobic members to a dimension smaller than a gap through which the first liquid and the second liquid pass.

15. The medical instrument according to claim 13, wherein the first base portion and the second base portion have a wire shape or a plate shape.

16. The medical instrument according to claim 13, wherein the elongated tubular peripheral wall is a shaft portion of a catheter, a sheath tube of a sheath, a stent, or a flow diverter stent.

17. The medical instrument according to claim 13, wherein the first braided layer is disposed on an outer surface of the second braided layer.

18. The medical instrument according to claim 13, wherein the second braided layer is disposed on an outer surface of the first braided layer.

19. A medical instrument comprising:

a main body portion having a lumen and a radially outward space partitioned by a tubular peripheral wall portion;

the tubular peripheral wall portion including at least:

a first layer having a hydrophilic member including a first base portion and a hydrophilic coating formed on the first base portion;

a second layer having a hydrophobic member including a second base portion and a hydrophobic coating formed on the second base portion; and the first layer and the second layer being stacked along a radial direction, and wherein one of the first layer and the second layer is coiled shape, and another of the first layer and the second layer is mesh shaped; and wherein when the hydrophilic coating is swollen, adjacent hydrophilic members come into contact with each other so that a first liquid in the lumen and a second liquid present in the radially outward space are prevented from circulating through the tubular peripheral wall portion.

* * * * *